US008352025B2

(12) United States Patent
Jacobson

(10) Patent No.: US 8,352,025 B2
(45) Date of Patent: *Jan. 8, 2013

(54) LEADLESS CARDIAC PACEMAKER TRIGGERED BY CONDUCTIVE COMMUNICATION

(75) Inventor: Peter M. Jacobson, Chanhassen, MN (US)

(73) Assignee: Nanostim, Inc., Sunnyvale, CA (US)

( * ) Notice: Subject to any disclaimer, the term of this patent is extended or adjusted under 35 U.S.C. 154(b) by 778 days.

This patent is subject to a terminal disclaimer.

(21) Appl. No.: 11/549,596

(22) Filed: Oct. 13, 2006

(65) Prior Publication Data

US 2007/0088398 A1 Apr. 19, 2007

Related U.S. Application Data

(60) Provisional application No. 60/726,706, filed on Oct. 14, 2005, provisional application No. 60/729,671, filed on Oct. 24, 2005, provisional application No. 60/737,296, filed on Nov. 16, 2005, provisional application No. 60/739,901, filed on Nov. 26, 2005, provisional application No. 60/749,017, filed on Dec. 10, 2005, provisional application No. 60/761,531, filed on Jan. 24, 2006, provisional application No. 60/761,740, filed on Jan. 24, 2006.

(51) Int. Cl.
*A61N 1/00* (2006.01)

(52) U.S. Cl. .................................. 607/2; 607/9

(58) Field of Classification Search .......... 600/508–509; 607/2–9, 33, 36–37
See application file for complete search history.

(56) References Cited

U.S. PATENT DOCUMENTS

| 3,199,508 A | 8/1965 | Roth |
| 3,212,496 A | 10/1965 | Preston |
| 3,218,638 A | 11/1965 | Honig |
| 3,241,556 A | 3/1966 | Zacouto |
| 3,478,746 A | 11/1969 | Greatbatch |
| 3,603,881 A | 9/1971 | Thornton |
| 3,727,616 A | 4/1973 | Lenzkes |
| 3,757,778 A | 9/1973 | Graham |
| 3,823,708 A | 7/1974 | Lawhorn |
| 3,830,228 A | 8/1974 | Foner |
| 3,835,864 A | 9/1974 | Rasor et al. |
| 3,836,798 A | 9/1974 | Greatbatch |
| 3,870,051 A | 3/1975 | Brindley |
| 3,872,251 A | 3/1975 | Auerbach et al. |
| 3,905,364 A | 9/1975 | Cudahy et al. |
| 3,940,692 A | 2/1976 | Neilson et al. |
| 3,943,926 A | 3/1976 | Barragan |
| 3,943,936 A | 3/1976 | Rasor et al. |
| 3,946,744 A | 3/1976 | Auerbach |

(Continued)

FOREIGN PATENT DOCUMENTS

EP 1741465 A1 1/2007

(Continued)

OTHER PUBLICATIONS

PCT International Search Report dated Apr. 8, 2008.

(Continued)

*Primary Examiner* — Rex R Holmes
(74) *Attorney, Agent, or Firm* — Shay Glenn LLP

(57) ABSTRACT

A leadless cardiac pacemaker configured for implantation in electrical contact with a left ventricular cardiac chamber and configured for leadless triggered left-ventricular pacing for cardiac resynchronization therapy (CRT) in response to conducted signals from a pulse generator.

29 Claims, 11 Drawing Sheets

U.S. PATENT DOCUMENTS

| | | |
|---|---|---|
| 3,952,750 A | 4/1976 | Mirowski et al. |
| 4,027,663 A | 6/1977 | Fischler et al. |
| 4,072,154 A | 2/1978 | Anderson et al. |
| 4,083,366 A | 4/1978 | Gombrich et al. |
| 4,102,344 A | 7/1978 | Conway et al. |
| 4,146,029 A | 3/1979 | Ellinwood, Jr. |
| 4,151,513 A | 4/1979 | Menken et al. |
| 4,151,540 A | 4/1979 | Sander et al. |
| 4,152,540 A | 5/1979 | Duncan et al. |
| 4,173,221 A | 11/1979 | McLaughlin et al. |
| 4,187,854 A | 2/1980 | Hepp et al. |
| 4,210,149 A | 7/1980 | Heilman et al. |
| RE30,366 E | 8/1980 | Rasor et al. |
| 4,223,678 A | 9/1980 | Langer et al. |
| 4,250,888 A | 2/1981 | Grosskopf |
| 4,256,115 A | 3/1981 | Bilitch |
| 4,296,756 A | 10/1981 | Dunning et al. |
| 4,310,000 A | 1/1982 | Lindemans |
| 4,318,412 A | 3/1982 | Stanly et al. |
| 4,336,810 A | 6/1982 | Anderson et al. |
| 4,350,169 A | 9/1982 | Dutcher et al. |
| 4,374,382 A | 2/1983 | Markowitz |
| 4,406,288 A | 9/1983 | Horwinski et al. |
| 4,411,271 A | 10/1983 | Markowitz |
| 4,418,695 A | 12/1983 | Buffet |
| 4,424,551 A | 1/1984 | Stevenson et al. |
| 4,428,378 A | 1/1984 | Anderson et al. |
| 4,440,173 A | 4/1984 | Hudziak et al. |
| 4,442,840 A | 4/1984 | Wojciechowicz, Jr. |
| 4,453,162 A | 6/1984 | Money et al. |
| 4,481,950 A | 11/1984 | Duggan |
| 4,513,743 A | 4/1985 | van Arragon et al. |
| 4,516,579 A | 5/1985 | Irnich |
| 4,522,208 A | 6/1985 | Buffet |
| 4,524,774 A | 6/1985 | Hildebrandt |
| 4,531,527 A | 7/1985 | Reinhold, Jr. et al. |
| 4,543,955 A | 10/1985 | Schroeppel |
| 4,550,370 A | 10/1985 | Baker |
| 4,552,127 A | 11/1985 | Schiff |
| 4,552,154 A | 11/1985 | Hartlaub |
| 4,562,846 A | 1/1986 | Cox et al. |
| 4,586,508 A | 5/1986 | Batina et al. |
| 4,606,352 A | 8/1986 | Geddes et al. |
| 4,607,639 A | 8/1986 | Tanagho et al. |
| 4,612,934 A | 9/1986 | Borkan |
| 4,625,730 A | 12/1986 | Fountain et al. |
| 4,679,144 A | 7/1987 | Cox et al. |
| 4,681,111 A | 7/1987 | Silvian |
| 4,681,117 A | 7/1987 | Brodman et al. |
| 4,702,253 A | 10/1987 | Nappholz et al. |
| 4,719,920 A | 1/1988 | Alt et al. |
| 4,722,342 A | 2/1988 | Amundson |
| 4,750,495 A | 6/1988 | Moore et al. |
| 4,763,340 A | 8/1988 | Yoneda et al. |
| 4,763,655 A | 8/1988 | Wirtzfeld et al. |
| 4,787,389 A | 11/1988 | Tarjan |
| 4,791,931 A | 12/1988 | Slate |
| 4,793,353 A | 12/1988 | Borkan |
| 4,794,532 A | 12/1988 | Leckband et al. |
| 4,802,481 A | 2/1989 | Schroeppel |
| 4,809,697 A | 3/1989 | Causey, III et al. |
| 4,827,940 A | 5/1989 | Mayer et al. |
| 4,830,006 A | 5/1989 | Haluska et al. |
| 4,844,076 A | 7/1989 | Lesho et al. |
| 4,846,195 A | 7/1989 | Alt |
| 4,860,750 A | 8/1989 | Frey et al. |
| 4,875,483 A | 10/1989 | Vollmann et al. |
| 4,880,004 A | 11/1989 | Baker, Jr. et al. |
| 4,883,064 A | 11/1989 | Olson et al. |
| 4,886,064 A | 12/1989 | Strandberg |
| 4,896,068 A | 1/1990 | Nilsson |
| 4,903,701 A | 2/1990 | Moore et al. |
| 4,905,708 A | 3/1990 | Davies |
| 4,926,863 A | 5/1990 | Alt |
| 4,974,589 A | 12/1990 | Sholder |
| 4,987,897 A * | 1/1991 | Funke ............................ 607/32 |
| 4,995,390 A | 2/1991 | Cook et al. |
| 5,010,887 A | 4/1991 | Thornander |
| 5,012,806 A | 5/1991 | De Bellis |
| 5,014,700 A | 5/1991 | Alt |
| 5,014,701 A | 5/1991 | Pless et al. |
| 5,031,615 A | 7/1991 | Alt |
| 5,040,533 A | 8/1991 | Fearnot |
| 5,040,534 A | 8/1991 | Mann et al. |
| 5,040,536 A | 8/1991 | Riff |
| 5,042,497 A | 8/1991 | Shapland |
| 5,052,399 A | 10/1991 | Olive et al. |
| 5,058,581 A | 10/1991 | Silvian |
| 5,065,759 A | 11/1991 | Begemann |
| 5,076,270 A | 12/1991 | Stutz, Jr. |
| 5,076,272 A | 12/1991 | Ferek-Petric |
| 5,085,224 A | 2/1992 | Galen et al. |
| 5,086,772 A | 2/1992 | Larnard et al. |
| 5,088,488 A | 2/1992 | Markowitz et al. |
| 5,095,903 A | 3/1992 | DeBellis |
| 5,109,845 A | 5/1992 | Yuuchi et al. |
| 5,111,816 A | 5/1992 | Pless et al. |
| 5,113,859 A | 5/1992 | Funke |
| 5,113,869 A | 5/1992 | Nappholz et al. |
| 5,133,350 A | 7/1992 | Duffin |
| 5,135,004 A | 8/1992 | Adams et al. |
| 5,170,784 A | 12/1992 | Ramon et al. |
| 5,170,802 A | 12/1992 | Mehra |
| 5,179,947 A | 1/1993 | Meyerson et al. |
| 5,184,616 A * | 2/1993 | Weiss ............................... 607/4 |
| 5,193,539 A | 3/1993 | Schulman et al. |
| 5,193,540 A | 3/1993 | Schulman et al. |
| 5,193,550 A | 3/1993 | Duffin |
| 5,217,010 A | 6/1993 | Tsitlik et al. |
| 5,247,945 A | 9/1993 | Heinze et al. |
| 5,259,394 A | 11/1993 | Bens |
| 5,267,150 A | 11/1993 | Wilkinson |
| 5,282,841 A | 2/1994 | Szyszkowski |
| 5,284,136 A | 2/1994 | Hauck et al. |
| 5,291,902 A | 3/1994 | Carman |
| 5,300,093 A | 4/1994 | Koestner et al. |
| 5,304,206 A | 4/1994 | Baker, Jr. et al. |
| 5,304,209 A | 4/1994 | Adams et al. |
| 5,313,953 A | 5/1994 | Yomtov et al. |
| 5,318,596 A | 6/1994 | Barreras et al. |
| 5,324,316 A | 6/1994 | Schulman et al. |
| 5,331,966 A | 7/1994 | Bennett et al. |
| 5,333,095 A | 7/1994 | Stevenson et al. |
| 5,342,401 A | 8/1994 | Spano et al. |
| 5,354,317 A | 10/1994 | Alt |
| 5,358,514 A | 10/1994 | Schulman et al. |
| 5,373,852 A | 12/1994 | Harrison et al. |
| 5,383,912 A | 1/1995 | Cox et al. |
| 5,383,915 A | 1/1995 | Adams |
| 5,404,877 A | 4/1995 | Nolan et al. |
| 5,405,367 A | 4/1995 | Schulman et al. |
| 5,406,444 A | 4/1995 | Selfried et al. |
| 5,411,532 A | 5/1995 | Mortazavi |
| 5,411,535 A | 5/1995 | Fuji et al. |
| 5,411,537 A | 5/1995 | Munshi et al. |
| 5,417,222 A | 5/1995 | Dempsey et al. |
| 5,419,337 A | 5/1995 | Dempsey et al. |
| 5,431,171 A | 7/1995 | Harrison et al. |
| 5,446,447 A | 8/1995 | Carney et al. |
| 5,456,261 A | 10/1995 | Luczyk |
| 5,466,246 A | 11/1995 | Silvian |
| 5,469,857 A | 11/1995 | Laurent et al. |
| 5,480,415 A | 1/1996 | Cox et al. |
| 5,481,262 A | 1/1996 | Urbas et al. |
| 5,522,876 A | 6/1996 | Rusink |
| 5,531,779 A | 7/1996 | Dahl et al. |
| 5,531,781 A | 7/1996 | Alferness et al. |
| 5,531,783 A | 7/1996 | Giele et al. |
| 5,539,775 A | 7/1996 | Tuttle et al. |
| 5,549,654 A | 8/1996 | Powell |
| 5,549,659 A | 8/1996 | Johansen et al. |
| 5,551,427 A | 9/1996 | Altman |
| 5,556,421 A | 9/1996 | Prutchi et al. |
| 5,562,717 A | 10/1996 | Tippey et al. |
| 5,571,143 A | 11/1996 | Hoegnelid et al. |
| 5,571,148 A | 11/1996 | Loeb et al. |
| 5,579,775 A | 12/1996 | Dempsey et al. |

| Patent | Date | Inventor |
|---|---|---|
| 5,586,556 A | 12/1996 | Spivey et al. |
| 5,591,217 A | 1/1997 | Barreras |
| 5,598,848 A | 2/1997 | Swanson et al. |
| 5,649,952 A | 7/1997 | Lam |
| 5,650,759 A | 7/1997 | Hittman et al. |
| 5,654,984 A | 8/1997 | Hershbarger et al. |
| 5,662,689 A | 9/1997 | Elsberry et al. |
| 5,669,391 A | 9/1997 | Williams |
| 5,674,259 A | 10/1997 | Gray |
| 5,676,153 A | 10/1997 | Smith et al. |
| 5,693,076 A | 12/1997 | Kaemmerer |
| 5,694,940 A | 12/1997 | Unger et al. |
| 5,694,952 A | 12/1997 | Lidman et al. |
| 5,697,958 A | 12/1997 | Paul et al. |
| 5,702,427 A | 12/1997 | Ecker et al. |
| 5,725,559 A | 3/1998 | Alt et al. |
| 5,728,154 A | 3/1998 | Crossett et al. |
| 5,730,143 A | 3/1998 | Schwarzberg |
| 5,735,880 A | 4/1998 | Prutchi et al. |
| 5,738,102 A | 4/1998 | Lemelson |
| 5,740,811 A | 4/1998 | Hedberg et al. |
| 5,741,314 A | 4/1998 | Daly et al. |
| 5,766,231 A | 6/1998 | Erickson et al. |
| 5,792,205 A | 8/1998 | Alt et al. |
| 5,810,735 A | 9/1998 | Halperin et al. |
| 5,814,076 A | 9/1998 | Brownlee |
| 5,814,087 A | 9/1998 | Renirie |
| 5,814,089 A | 9/1998 | Stokes et al. |
| 5,824,016 A | 10/1998 | Ekwall |
| 5,871,451 A | 2/1999 | Unger et al. |
| 5,876,353 A | 3/1999 | Riff |
| 5,876,425 A | 3/1999 | Gord et al. |
| 5,891,178 A | 4/1999 | Mann et al. |
| 5,899,928 A | 5/1999 | Sholder et al. |
| 5,935,079 A | 8/1999 | Swanson et al. |
| 5,954,761 A | 9/1999 | Machek et al. |
| 5,957,861 A | 9/1999 | Combs et al. |
| 5,984,861 A | 11/1999 | Crowley |
| 5,987,352 A | 11/1999 | Klein et al. |
| 5,995,876 A | 11/1999 | Kruse et al. |
| 5,999,857 A | 12/1999 | Weijand et al. |
| 6,002,969 A | 12/1999 | Machek et al. |
| 6,004,269 A | 12/1999 | Crowley et al. |
| 6,061,596 A | 5/2000 | Richmond et al. |
| 6,076,016 A | 6/2000 | Feierbach |
| 6,080,187 A | 6/2000 | Alt et al. |
| 6,093,146 A | 7/2000 | Filangeri |
| 6,096,065 A | 8/2000 | Crowley |
| 6,102,874 A | 8/2000 | Stone et al. |
| 6,112,116 A | 8/2000 | Fischell et al. |
| 6,115,628 A | 9/2000 | Stadler et al. |
| 6,115,630 A | 9/2000 | Stadler et al. |
| 6,115,636 A | 9/2000 | Ryan |
| 6,119,031 A | 9/2000 | Crowley |
| 6,125,290 A | 9/2000 | Miesel |
| 6,125,291 A | 9/2000 | Miesel et al. |
| 6,128,526 A | 10/2000 | Stadler et al. |
| 6,129,751 A | 10/2000 | Lucchesi et al. |
| 6,132,390 A | 10/2000 | Cookston et al. |
| 6,132,456 A | 10/2000 | Sommer et al. |
| 6,134,459 A | 10/2000 | Roberts et al. |
| 6,134,470 A | 10/2000 | Hartlaub |
| 6,139,510 A | 10/2000 | Palermo |
| 6,141,584 A | 10/2000 | Rockwell et al. |
| 6,141,588 A | 10/2000 | Cox et al. |
| 6,141,592 A | 10/2000 | Pauly |
| 6,144,866 A | 11/2000 | Miesel et al. |
| 6,148,230 A | 11/2000 | KenKnight |
| 6,152,882 A | 11/2000 | Prutchi |
| 6,163,723 A | 12/2000 | Roberts et al. |
| 6,164,284 A | 12/2000 | Schulman et al. |
| 6,167,310 A | 12/2000 | Grevious |
| 6,178,349 B1 | 1/2001 | Kieval |
| 6,178,356 B1 | 1/2001 | Chastain et al. |
| 6,185,443 B1 | 2/2001 | Crowley |
| 6,185,452 B1 | 2/2001 | Schulman et al. |
| 6,185,464 B1 | 2/2001 | Bonner et al. |
| 6,188,932 B1 | 2/2001 | Lindegren |
| 6,190,324 B1 | 2/2001 | Kieval et al. |
| 6,198,952 B1 | 3/2001 | Miesel |
| 6,201,993 B1 | 3/2001 | Kruse et al. |
| 6,208,894 B1 | 3/2001 | Schulman et al. |
| 6,208,900 B1 | 3/2001 | Ecker et al. |
| 6,223,081 B1 | 4/2001 | Kerver |
| 6,230,059 B1 | 5/2001 | Duffin |
| 6,236,882 B1 | 5/2001 | Lee et al. |
| 6,240,321 B1 | 5/2001 | Janke et al. |
| 6,243,608 B1 | 6/2001 | Pauly et al. |
| 6,248,080 B1 | 6/2001 | Miesel et al. |
| 6,263,245 B1 | 7/2001 | Snell |
| 6,265,100 B1 | 7/2001 | Saaski et al. |
| 6,266,554 B1 | 7/2001 | Hsu et al. |
| 6,272,379 B1 | 8/2001 | Fischell et al. |
| 6,280,409 B1 | 8/2001 | Stone et al. |
| 6,289,229 B1 | 9/2001 | Crowley |
| 6,306,088 B1 | 10/2001 | Krausman et al. |
| 6,310,960 B1 | 10/2001 | Saaski et al. |
| 6,315,721 B2 | 11/2001 | Schulman et al. |
| 6,324,418 B1 | 11/2001 | Crowley et al. |
| 6,324,421 B1 | 11/2001 | Stadler et al. |
| RE37,463 E | 12/2001 | Altman |
| 6,343,227 B1 | 1/2002 | Crowley |
| 6,343,233 B1 | 1/2002 | Werner et al. |
| 6,347,245 B1 | 2/2002 | Lee et al. |
| 6,358,202 B1 | 3/2002 | Arent |
| 6,361,522 B1 | 3/2002 | Scheiner et al. |
| 6,363,282 B1 | 3/2002 | Nichols et al. |
| 6,364,831 B1 | 4/2002 | Crowley |
| 6,370,434 B1 | 4/2002 | Zhang et al. |
| 6,381,492 B1 | 4/2002 | Rockwell et al. |
| 6,381,493 B1 | 4/2002 | Stadler et al. |
| 6,381,494 B1 | 4/2002 | Gilkerson et al. |
| 6,383,209 B1 | 5/2002 | Crowley |
| 6,385,593 B2 | 5/2002 | Linberg |
| 6,386,882 B1 | 5/2002 | Linberg |
| 6,397,100 B2 | 5/2002 | Stadler et al. |
| 6,402,689 B1 | 6/2002 | Scarantino et al. |
| 6,405,073 B1 | 6/2002 | Crowley et al. |
| 6,405,083 B1 | 6/2002 | Rockwell et al. |
| 6,409,674 B1 | 6/2002 | Brockway et al. |
| 6,409,675 B1 | 6/2002 | Turcott |
| 6,412,490 B1 | 7/2002 | Lee |
| 6,418,346 B1 | 7/2002 | Nelson et al. |
| 6,423,056 B1 | 7/2002 | Ishikawa et al. |
| 6,424,866 B2 | 7/2002 | Mika et al. |
| 6,428,484 B1 | 8/2002 | Battmer et al. |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,442,433 B1 | 8/2002 | Linberg |
| 6,444,970 B1 | 9/2002 | Barbato |
| 6,445,953 B1 | 9/2002 | Bulkes et al. |
| 6,458,145 B1 | 10/2002 | Ravenscroft et al. |
| 6,459,928 B2 | 10/2002 | Mika et al. |
| 6,459,937 B1 | 10/2002 | Morgan et al. |
| 6,466,820 B1 | 10/2002 | Juran et al. |
| 6,468,263 B1 | 10/2002 | Fischell et al. |
| 6,470,215 B1 | 10/2002 | Kraus et al. |
| 6,471,645 B1 | 10/2002 | Warkentin et al. |
| 6,472,991 B1 | 10/2002 | Schulman et al. |
| 6,477,424 B1 | 11/2002 | Thompson et al. |
| 6,480,733 B1 | 11/2002 | Turcott |
| 6,482,154 B1 | 11/2002 | Haubrich et al. |
| 6,484,055 B1 | 11/2002 | Marcovecchio |
| 6,484,057 B2 | 11/2002 | Ideker et al. |
| 6,490,487 B1 | 12/2002 | Kraus et al. |
| 6,496,715 B1 | 12/2002 | Lee et al. |
| 6,500,168 B1 | 12/2002 | Jellie |
| 6,501,983 B1 | 12/2002 | Natarajan et al. |
| 6,512,949 B1 | 1/2003 | Combs et al. |
| 6,512,959 B1 | 1/2003 | Gomperz et al. |
| 6,522,926 B1 | 2/2003 | Kieval et al. |
| 6,522,928 B2 | 2/2003 | Whitehurst et al. |
| 6,539,257 B1 | 3/2003 | KenKnight |
| 6,556,860 B1 | 4/2003 | Groenewegen |
| 6,558,321 B1 | 5/2003 | Burd et al. |
| 6,564,807 B1 | 5/2003 | Schulman et al. |
| 6,567,680 B2 | 5/2003 | Swetlik et al. |

| | | | | | | |
|---|---|---|---|---|---|---|
| 6,571,120 B2 | 5/2003 | Hutten | 6,882,875 B1 | 4/2005 | Crowley | |
| 6,574,509 B1 | 6/2003 | Kraus et al. | 6,889,081 B2 | 5/2005 | Hsu | |
| 6,574,511 B2 | 6/2003 | Lee | 6,893,395 B1 | 5/2005 | Kraus et al. | |
| 6,580,946 B2 | 6/2003 | Struble | 6,895,279 B2 | 5/2005 | Loeb et al. | |
| 6,580,948 B2 | 6/2003 | Haupert et al. | 6,895,281 B1 | 5/2005 | Amundson et al. | |
| 6,584,351 B1 | 6/2003 | Ekwall | 6,896,651 B2 | 5/2005 | Gross et al. | |
| 6,584,352 B2 | 6/2003 | Combs et al. | 6,897,788 B2 | 5/2005 | Khair et al. | |
| 6,589,187 B1 | 7/2003 | Dirnberger et al. | 6,901,294 B1 | 5/2005 | Whitehurst et al. | |
| 6,592,518 B2 | 7/2003 | Denker et al. | 6,901,296 B1 | 5/2005 | Whitehurst et al. | |
| 6,594,523 B1 | 7/2003 | Levine | 6,907,285 B2 | 6/2005 | Denker et al. | |
| 6,597,948 B1 | 7/2003 | Rockwell et al. | 6,907,293 B2 | 6/2005 | Grill et al. | |
| 6,597,952 B1 | 7/2003 | Mika et al. | 6,912,420 B2 | 6/2005 | Scheiner et al. | |
| 6,609,023 B1 | 8/2003 | Fischell et al. | 6,917,833 B2 | 7/2005 | Denker et al. | |
| 6,611,710 B2 | 8/2003 | Gomperz et al. | 6,925,328 B2 | 8/2005 | Foster et al. | |
| 6,615,075 B2 | 9/2003 | Mlynash et al. | 6,931,327 B2 | 8/2005 | Goode, Jr. et al. | |
| 6,622,043 B1 | 9/2003 | Kraus et al. | 6,999,821 B2 | 2/2006 | Jenney et al. | |
| 6,647,292 B1 | 11/2003 | Bardy et al. | 7,001,372 B2 | 2/2006 | Richter | |
| 6,648,823 B2 | 11/2003 | Thompson | 7,023,359 B2 | 4/2006 | Goetz et al. | |
| 6,649,078 B2 | 11/2003 | Yu | 7,146,222 B2 | 12/2006 | Boling | |
| 6,654,638 B1 | 11/2003 | Sweeney | 7,146,225 B2 | 12/2006 | Guenst et al. | |
| 6,658,285 B2 | 12/2003 | Potse et al. | 7,164,950 B2 | 1/2007 | Kroll et al. | |
| 6,658,297 B2 | 12/2003 | Loeb | 7,181,505 B2 | 2/2007 | Haller et al. | |
| 6,658,301 B2 | 12/2003 | Loeb et al. | 7,187,971 B2 | 3/2007 | Sommer et al. | |
| 6,659,959 B2 | 12/2003 | Brockway et al. | 7,200,437 B1 * | 4/2007 | Nabutovsky et al. | 607/9 |
| 6,669,631 B2 | 12/2003 | Norris et al. | 7,212,870 B1 | 5/2007 | Helland | |
| 6,681,135 B1 | 1/2004 | Davis et al. | 7,289,853 B1 | 10/2007 | Campbell et al. | |
| 6,684,100 B1 | 1/2004 | Sweeney et al. | 7,363,090 B2 | 4/2008 | Halperin et al. | |
| 6,687,540 B2 | 2/2004 | Marcovecchio | 7,558,631 B2 | 7/2009 | Cowan et al. | |
| 6,687,546 B2 | 2/2004 | Lebel et al. | 7,565,195 B1 * | 7/2009 | Kroll et al. | 607/2 |
| 6,689,117 B2 | 2/2004 | Sweeney et al. | 7,616,991 B2 | 11/2009 | Mann et al. | |
| 6,690,959 B2 | 2/2004 | Thompson | 7,630,767 B1 | 12/2009 | Poore et al. | |
| 6,694,191 B2 | 2/2004 | Starkweather et al. | 7,634,313 B1 | 12/2009 | Kroll et al. | |
| 6,695,885 B2 | 2/2004 | Schulman et al. | 2001/0031999 A1 | 10/2001 | Carter et al. | |
| 6,697,672 B2 | 2/2004 | Andersson | 2002/0077686 A1 | 6/2002 | Westlund et al. | |
| 6,699,200 B2 | 3/2004 | Cao et al. | 2002/0116028 A1 | 8/2002 | Greatbatch et al. | |
| 6,702,857 B2 | 3/2004 | Brauker et al. | 2002/0147488 A1 | 10/2002 | Doan et al. | |
| 6,704,602 B2 | 3/2004 | Berg et al. | 2003/0158584 A1 | 8/2003 | Cates et al. | |
| 6,711,440 B2 | 3/2004 | Deal et al. | 2003/0163184 A1 | 8/2003 | Schiener | |
| 6,721,597 B1 | 4/2004 | Bardy et al. | 2004/0011366 A1 | 1/2004 | Schulman et al. | |
| 6,728,572 B2 | 4/2004 | Hsu et al. | 2004/0059392 A1 | 3/2004 | Parramon et al. | |
| 6,728,574 B2 | 4/2004 | Ujhelyi et al. | 2004/0116939 A1 | 6/2004 | Goode | |
| 6,731,976 B2 | 5/2004 | Penn et al. | 2004/0133242 A1 | 7/2004 | Chapman et al. | |
| 6,731,979 B2 | 5/2004 | MacDonald | 2004/0143262 A1 | 7/2004 | Visram et al. | |
| 6,733,485 B1 | 5/2004 | Whitehurst et al. | 2004/0147973 A1 | 7/2004 | Hauser | |
| 6,735,474 B1 | 5/2004 | Loeb et al. | 2004/0167587 A1 | 8/2004 | Thompson | |
| 6,735,475 B1 | 5/2004 | Whitehurst et al. | 2004/0172116 A1 | 9/2004 | Seifert et al. | |
| 6,738,670 B1 | 5/2004 | Almendinger et al. | 2004/0193223 A1 | 9/2004 | Kramer et al. | |
| 6,741,877 B1 | 5/2004 | Shults et al. | 2004/0249417 A1 | 12/2004 | Ransbury et al. | |
| 6,741,886 B2 | 5/2004 | Yonce | 2004/0260349 A1 | 12/2004 | Stroebel | |
| 6,746,404 B2 | 6/2004 | Schwartz | 2005/0038474 A1 | 2/2005 | Wool | |
| 6,754,538 B2 | 6/2004 | Linberg | 2005/0043765 A1 | 2/2005 | Williams et al. | |
| 6,760,620 B2 | 7/2004 | Sippens Groenewegen | 2005/0075682 A1 | 4/2005 | Schulman et al. | |
| 6,764,446 B2 | 7/2004 | Wolinsky et al. | 2005/0096702 A1 | 5/2005 | Denker et al. | |
| 6,768,923 B2 | 7/2004 | Ding et al. | 2005/0131478 A1 | 6/2005 | Kim et al. | |
| 6,783,499 B2 | 8/2004 | Schwartz | 2005/0149138 A1 * | 7/2005 | Min et al. | 607/27 |
| 6,785,576 B2 | 8/2004 | Verness | 2005/0165465 A1 | 7/2005 | Pianca et al. | |
| 6,786,860 B2 | 9/2004 | Maltan et al. | 2005/0267555 A1 | 12/2005 | Marnfeldt et al. | |
| 6,792,314 B2 | 9/2004 | Byers et al. | 2005/0288722 A1 | 12/2005 | Eigler et al. | |
| 6,799,069 B2 | 9/2004 | Weiner et al. | 2006/0085039 A1 | 4/2006 | Hastings et al. | |
| 6,804,559 B1 | 10/2004 | Kraus et al. | 2006/0085041 A1 | 4/2006 | Hastings et al. | |
| 6,804,561 B2 | 10/2004 | Stover | 2006/0085042 A1 | 4/2006 | Hastings et al. | |
| 6,809,507 B2 | 10/2004 | Morgan et al. | 2006/0121475 A1 | 6/2006 | Davids et al. | |
| 6,811,533 B2 | 11/2004 | Lebel et al. | 2006/0135999 A1 | 6/2006 | Bodner et al. | |
| 6,813,519 B2 | 11/2004 | Lebel et al. | 2006/0136004 A1 | 6/2006 | Cowan et al. | |
| 6,821,154 B1 | 11/2004 | Canfield et al. | 2006/0161222 A1 | 7/2006 | Haubrich et al. | |
| 6,823,217 B2 | 11/2004 | Rutten et al. | 2006/0241705 A1 | 10/2006 | Neumann et al. | |
| 6,824,512 B2 | 11/2004 | Warkentin et al. | 2006/0247750 A1 | 11/2006 | Seifert et al. | |
| 6,829,508 B2 | 12/2004 | Schulman et al. | 2006/0282150 A1 | 12/2006 | Olson et al. | |
| 6,839,596 B2 | 1/2005 | Nelson et al. | 2007/0016263 A1 | 1/2007 | Armstrong et al. | |
| 6,848,052 B1 | 1/2005 | Hamid et al. | 2007/0043414 A1 | 2/2007 | Fifer et al. | |
| 6,850,801 B2 | 2/2005 | Kieval et al. | 2007/0088394 A1 | 4/2007 | Jacobson | |
| 6,862,465 B2 | 3/2005 | Shults et al. | 2007/0088396 A1 | 4/2007 | Jacobson | |
| 6,862,480 B2 | 3/2005 | Cohen et al. | 2007/0088397 A1 | 4/2007 | Jacobson | |
| 6,865,420 B1 | 3/2005 | Kroll | 2007/0088400 A1 | 4/2007 | Jacobson | |
| 6,869,404 B2 | 3/2005 | Schulhauser et al. | 2007/0088405 A1 | 4/2007 | Jacobson | |
| 6,871,099 B1 | 3/2005 | Whitehurst et al. | 2007/0088418 A1 | 4/2007 | Jacobson | |
| 6,878,112 B2 | 4/2005 | Linberg et al. | 2007/0123923 A1 | 5/2007 | Lindstrom et al. | |
| 6,879,695 B2 | 4/2005 | Maltan et al. | 2007/0142709 A1 | 6/2007 | Martone et al. | |
| 6,879,855 B2 | 4/2005 | Schulman et al. | 2007/0179552 A1 | 8/2007 | Dennis et al. | |

| | | | |
|---|---|---|---|
| 2007/0270675 | A1 | 11/2007 | Kane et al. |
| 2007/0276004 | A1 | 11/2007 | Hirsch et al. |
| 2007/0276444 | A1 | 11/2007 | Gelbart et al. |
| 2007/0293904 | A1 | 12/2007 | Gelbart et al. |
| 2008/0004535 | A1 | 1/2008 | Smits |
| 2008/0021532 | A1 | 1/2008 | Kveen et al. |
| 2008/0039738 | A1 | 2/2008 | Dinsmoor et al. |
| 2008/0086168 | A1 | 4/2008 | Cahill |
| 2008/0119911 | A1 | 5/2008 | Rosero |
| 2008/0269591 | A1 | 10/2008 | Halperin et al. |
| 2009/0082828 | A1 | 3/2009 | Ostroff |
| 2009/0149902 | A1 | 6/2009 | Kumar et al. |
| 2009/0171408 | A1 | 7/2009 | Solem |
| 2010/0305656 | A1 | 12/2010 | Imran et al. |
| 2011/0208260 | A1 | 8/2011 | Jacobson |
| 2011/0218587 | A1 | 9/2011 | Jacobson |

FOREIGN PATENT DOCUMENTS

| | | |
|---|---|---|
| JP | 05-245215 | 9/1993 |
| JP | 06/507096 | 3/2006 |
| JP | 06/516449 | 7/2006 |
| WO | WO 98/37926 A1 | 9/1998 |
| WO | WO2004/012811 | 2/2004 |
| WO | WO 2006/065394 A1 | 6/2006 |
| WO | WO 2007/047681 A2 | 4/2007 |
| WO | WO 2007/059386 A2 | 5/2007 |

OTHER PUBLICATIONS

U.S. Appl. No. 10/891,747, filed Jul. 14, 2004, now abandoned (CIP of US Patent No. 7,630,767 B1, Dec. 8, 2009).

Beeby et al.; Micromachined silicon generator for harvesting power from vibrations; (Proceedings) PowerMEMS 2004; Kyoto, Japan; pp. 104-107; Nov. 28-30, 2004.

Brown, Eric S.; The atomic battery; Technology Review: Published by MIT; 4 pgs.; Jun. 16, 2005.

Irnich et al.; Do we need pacemakers resistant to magnetic resonance imaging; Europace; vol. 7; pp. 353-365; 2005.

Irnich; Electronic security systems and active implantable medical devices; Journal of PACE; vol. 25; No. 8; pp. 1235-1258; Aug. 2002.

Luechinger et al.; Force and torque effects of a 1.5-tesla MRI scanner of cardiac pacemakers and ICDs; Journal of PACE; vol. 24; No. 2; pp. 199-205; Feb. 2001.

Luechinger et al.; In vivo heating of pacemaker leads during magnetic resonance imaging; European Heart Journal; vol. 26; pp. 376-383; 2005.

Lüchinger ; Safety aspects of cardiac pacemakers in magnetic resonance imaging; Dissertation submitted to the Swiss Federal Institute of Technology Zurich; 2002.

Nyenhuis et al.; MRI and Implanted Medical Devices: Basic Interactions with an emphasis on heating; vol. 5; No. 3; pp. 467-480; Sep. 2005.

Ostroff, Alan; U.S. Appl. No. 12/568,513 entitled "MRI Compatible Leadless Cardiac Pacemaker," filed Sep. 28, 2009.

Ostroff, Alan; U.S. Appl. No. 12/698,969 entitled "Leadless Cardiac Pacemaker with Secondary Fixation Capability," filed Feb. 2, 2010.

Shellock et al.; Cardiac pacemaker: In vitro assessment at 1.5 T; Am Heart J; vol. 151; pp. 436-43; 2006.

Khairkhahan et al.; U.S. Appl. No. 13/272,074 entitled "Delivery catheter systems and methods," filed Oct. 12, 2011.

Khairkhahan et al.; U.S. Appl. No. 13/272,082 entitled "Leadless cardiac pacemaker with anti-unscrewing feature," filed Oct. 12, 2011.

Ostroff, Alan; U.S. Appl. No. 13/272,092 entitled "Temperature sensor for a leadless cardiac pacemaker," filed Oct. 12, 2011.

Khairkhaha et al.; U.S. Appl. No. 13/324,781 entitled "Delivery Catheter Systems and Methods," filed Dec. 13, 2011.

Jacobson et al.; U.S. Appl. No. 13/277,151 entitled "Leadless cardiac pacemaker with conducted communication," filed Oct. 19, 2011.

Khairkhahan et al.; U.S. Appl. No. 13/324,802 entitled "Pacemaker Retrieval Systems and Methods ," filed Dec. 13, 2011.

Khairkhahan et al.; U.S. Appl. No. 13/331,922 entitled "Leadless Pacemaker with Radial Fixation Mechanism ," filed Dec. 20, 2011.

Jacobson, Peter M.; U.S. Appl. No. 12/953,282 entitled "Leadless Cardiac Pacemaker Triggered by Conductive Communication," filed Nov. 23, 2010.

Jacobson, Peter M.; U.S. Appl. No. 13/191,229 entitled "Implantable biostimulator delivery system," filed Jul. 26, 2011.

Bordacher et al.; Impact and prevention of far-field sensing in fallback mode switches; PACE; vol. 26 (pt. II); pp. 206-209; 2003.

Brandt et al.; Far-field QRS complex sensing: prevalence and timing with bipolar atrial leads; PACE; vol. 23; pp. 315-320; 2000.

\* cited by examiner

LEADLESS CARDIAC PACEMAKER TRIGGERED BY CONDUCTIVE COMMUNICATION

CROSS REFERENCE TO RELATED APPLICATIONS

This application claims the benefit of priority to and incorporates herein by reference in its entirety for all purposes, Provisional U.S. Patent Application Nos. 60/726,706 entitled "LEADLESS CARDIAC PACEMAKER WITH CONDUCTED COMMUNICATION," filed Oct. 14, 2005; 60/761,531 entitled "LEADLESS CARDIAC PACEMAKER DELIVERY SYSTEM," filed Jan. 24, 2006; 60/729,671 entitled "LEADLESS CARDIAC PACEMAKER TRIGGERED BY CONDUCTED COMMUNICATION," filed Oct. 24, 2005; 60/737,296 entitled "SYSTEM OF LEADLESS CARDIAC PACEMAKERS WITH CONDUCTED COMMUNICATION," filed Nov. 16, 2005; 60/739,901 entitled "LEADLESS CARDIAC PACEMAKERS WITH CONDUCTED COMMUNICATION FOR USE WITH AN IMPLANTABLE CARDIOVERTER-DEFIBRILLATOR," filed Nov. 26, 2005; 60/749,017 entitled "LEADLESS CARDIAC PACEMAKER WITH CONDUCTED COMMUNICATION AND RATE RESPONSIVE PACING," filed Dec. 10, 2005; and 60/761,740 entitled "PROGRAMMER FOR A SYSTEM OF LEADLESS CARDIAC PACEMAKERS WITH CONDUCTED COMMUNICATION," filed Jan. 24, 2006; all by Peter M. Jacobson.

BACKGROUND

Cardiac pacing electrically stimulates the heart when the heart's natural pacemaker and/or conduction system fails to provide synchronized atrial and ventricular contractions at appropriate rates and intervals for a patient's needs. Such bradycardia pacing provides relief from symptoms and even life support for hundreds of thousands of patients. Cardiac pacing may also give electrical overdrive stimulation intended to suppress or convert tachyarrhythmias, again supplying relief from symptoms and preventing or terminating arrhythmias that could lead to sudden cardiac death.

Cardiac pacing is usually performed by a pulse generator implanted subcutaneously or sub-muscularly in or near a patient's pectoral region. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Recently, left-ventricular cardiac pacing has been practiced to ameliorate heart failure; a practice termed cardiac resynchronization therapy (CRT). CRT has been practiced with electrode-leads and a pulse generator, either an implantable cardioverter-defibrillator (CRT-D) or an otherwise conventional pacemaker (CRT-P). The left-ventricular pacing conventionally uses an electrode in contact with cardiac muscle in that chamber. The corresponding electrode-lead is usually placed endocardially in a transvenous manner through the coronary sinus vein, or epicardially.

Pulse generator parameters are usually interrogated and modified by a programming device outside the body, via a loosely-coupled transformer with one inductance within the body and another outside, or via electromagnetic radiation with one antenna within the body and another outside.

Although tens of thousands of left-ventricular electrode leads are implanted annually for use with separate pulse generators for CRT-D or CRT-P, various well-known difficulties are present.

A conventional pulse generator has an interface for connection to and disconnection from the electrode leads that carry signals to and from the heart. Usually at least one male connector molding has at least one terminal pin at the proximal end of the electrode lead. The at least one male connector mates with at least one corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover is typically included to provide electrical insulation of the setscrew. The complex connection between connectors and leads provides multiple opportunities for malfunction.

For example, failure to introduce the lead pin completely into the terminal block can prevent proper connection between the generator and electrode.

Failure to insert a screwdriver correctly through the setscrew slot, causing damage to the slot and subsequent insulation failure.

Failure to engage the screwdriver correctly in the setscrew can cause damage to the setscrew and preventing proper connection.

Failure to tighten the setscrew adequately also can prevent proper connection between the generator and electrode, however over-tightening of the setscrew can cause damage to the setscrew, terminal block, or lead pin, and prevent disconnection if necessary for maintenance.

Fluid leakage between the lead and generator connector moldings, or at the setscrew cover, can prevent proper electrical isolation.

Insulation or conductor breakage at a mechanical stress concentration point where the lead leaves the generator can also cause failure.

Inadvertent mechanical damage to the attachment of the connector molding to the generator can result in leakage or even detachment of the molding.

Inadvertent mechanical damage to the attachment of the connector molding to the lead body, or of the terminal pin to the lead conductor, can result in leakage, an open-circuit condition, or even detachment of the terminal pin and/or molding.

The lead body can be cut inadvertently during surgery by a tool, or cut after surgery by repeated stress on a ligature used to hold the lead body in position. Repeated movement for hundreds of millions of cardiac cycles can cause lead conductor breakage or insulation damage anywhere along the lead body.

Although leads are available commercially in various lengths, in some conditions excess lead length in a patient exists and is to be managed. Usually the excess lead is coiled near the pulse generator. Repeated abrasion between the lead body and the generator due to lead coiling can result in insulation damage to the lead.

Friction of the lead against the clavicle and the first rib, known as subclavian crush, can result in damage to the lead.

For CRT-D or CRT-P, multiple leads are implanted in the same patient and sometimes in the same vessel. Abrasion between the leads for hundreds of millions of cardiac cycles can cause insulation breakdown or even conductor failure.

SUMMARY

According to an embodiment of a biostimulation system, a leadless cardiac pacemaker is configured for implantation in electrical contact with a left ventricular cardiac chamber and configured for leadless triggered left-ventricular pacing for cardiac resynchronization therapy (CRT) in response to conducted signals from a pulse generator.

BRIEF DESCRIPTION OF THE DRAWINGS

Embodiments of the invention relating to both structure and method of operation may best be understood by referring to the following description and accompanying drawings, in which similar reference characters denote similar elements throughout the several views.

DETAILED DESCRIPTION

Figure 1A:
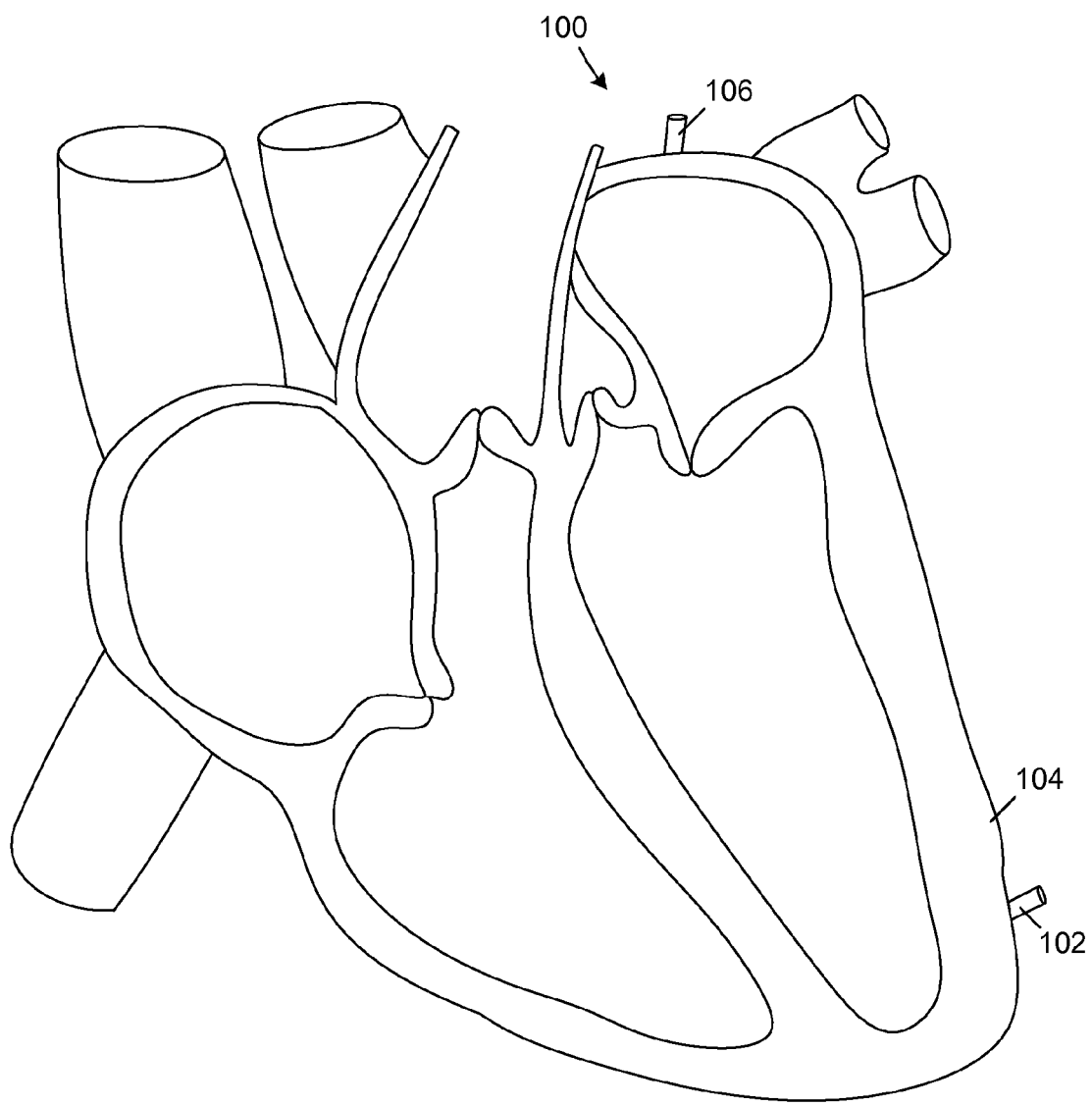
FIG. 1A is a pictorial diagram showing an embodiment of a cardiac pacing system that includes a leadless cardiac pacemaker which is triggered by conductive communication.

A leadless biostimulator can be triggered by conducted communication. For example, in a particular application, a leadless cardiac pacemaker can be triggered by conducted communication for pacing the left ventricle for CRT.

In some embodiments of a leadless biostimulator, a leadless left-ventricular cardiac pacemaker can be triggered by conducted communication, representing a substantial departure from the conventional CRT-D or CRT-P systems. For example, an illustrative cardiac pacing system can perform cardiac pacing, and in particular left-ventricular cardiac pacing for CRT-D or CRT-P, that has many of the advantages of conventional cardiac pacemakers while extending performance, functionality, and operating characteristics with one or more of several improvements.

In a particular embodiment of a cardiac pacing system, a left-ventricular cardiac pacemaker is configured for CRT-D or CRT-P operation without a left-ventricular electrode-lead connected to a separate pulse generator, without a communication coil or antenna, and without an additional requirement on battery power for transmitted communication.

An embodiment of a cardiac pacing system configured to attain these characteristics comprises a leadless cardiac pacemaker that is triggered by conducted communication and is substantially enclosed in a hermetic housing suitable for placement on or attachment to the inside or outside of a cardiac chamber, in particular the left ventricle. The leadless pacemaker has at least two electrodes located within, on, or near the housing, for delivering pacing pulses to muscle of the cardiac chamber and optionally for sensing electrical activity from the muscle, for receiving triggering signals from an implanted pulse generator, and optionally for bi-directional communication with at least one other device within or outside the body. The housing contains a primary battery to provide power for pacing, for receiving triggering signals, optionally for sensing, and optionally for bi-directional communication. The housing can optionally contain circuits for sensing cardiac activity from the electrodes. The housing contains circuits for receiving information from at least one other device via the electrodes and contains circuits for generating pacing pulses for delivery via the electrodes. The housing can optionally contain circuits for transmitting information to at least one other device via the electrodes and can optionally contain circuits for monitoring device health. The housing contains circuits for controlling these operations in a predetermined manner.

The conducted signal that triggers pacing in the leadless cardiac pacemaker can be any signal from a separate implanted pulse generator contained within the body and used with at least one electrode-lead. For example, the conducted signal can be a right-ventricular pacing pulse or atrial pacing pulse delivered by the implanted pulse generator. The implanted pulse generator may or may not include cardioversion and defibrillation functions so that a physician can use the leadless cardiac pacemaker to add left-ventricular pacing for CRT to an existing cardiac pacemaker or implantable cardioverter defibrillator. In some embodiments, a left-ventricular implanted leadless cardiac pacemaker can operate as a slave that is triggered by the atrial pacing pulse or right-ventricular pacing pulse of the separate pulse generator used for right-ventricular and/or atrial pacing.

In accordance with some embodiments, a cardiac pacemaker is adapted for implantation in the human body. In a particular embodiment, a leadless cardiac pacemaker can be adapted for implantation adjacent to the inside or outside wall of a cardiac chamber, using two or more electrodes located within, on, or within two centimeters of the housing of the pacemaker, for pacing the cardiac chamber upon receiving a triggering signal from at least one other device within the body.

In some embodiments, the cardiac pacing system can be configured for left-ventricular pacing in cardiac resynchronization therapy (CRT).

For example, some embodiments of a leadless pacemaker can be configured for implantation adjacent to the inside or outside wall of a cardiac chamber, in particular the left ventricle, without the need for a connection between the pulse generator and an electrode-lead, and without the need for a lead body.

In some examples, left-ventricular pacing can be triggered by conducted communication from another implanted pulse generator which is also implanted within the body such as by a right-ventricular pacing pulse or atrial pacing pulse from the other implanted pulse generator.

Other example embodiments optionally provide communication between the implanted leadless pacemaker and a programmer outside the body, or between the implanted leadless pacemaker and another pulse generator implanted within the body, using conducted communication via the same electrodes used for pacing, without the need for an antenna or telemetry coil.

Some example embodiments can to provide communication between the implanted leadless pacemaker and a programmer outside the body, or between the implanted leadless pacemaker and another pulse generator implanted within the body, with power requirements for the implanted leadless pacemaker similar to those for cardiac pacing, enabling optimization of battery performance.

Figure 1B:
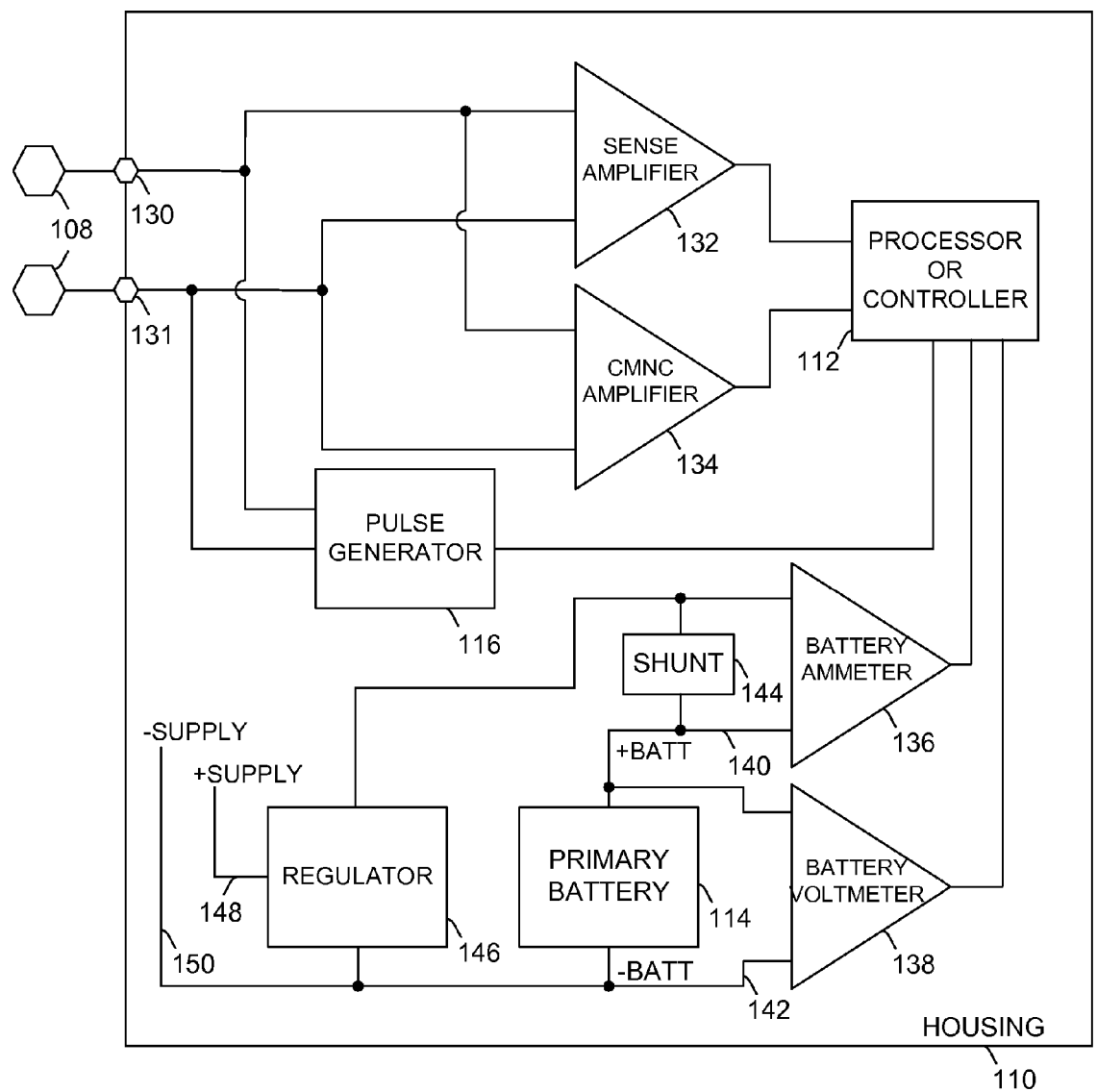
FIG. 1B is a schematic block diagram showing interconnection of operating elements of an embodiment of the illustrative stimulation system.

Referring to FIGS. 1A and 1B, a pictorial view which is not shown to scale and a schematic block diagram respectively depict an embodiment of a cardiac pacing system 100 that comprises a leadless cardiac pacemaker 102 configured for implantation in electrical contact with a left ventricular cardiac chamber 104 and for leadless triggered left-ventricular pacing for cardiac resynchronization therapy (CRT) in response to conducted signals from a pulse generator 106.

In a particular arrangement, the leadless cardiac pacemaker 102 can be configured for leadless triggered left-ventricular pacing in response to conducted signals from one or more implanted leadless or electrode-lead pulse generators 106. The system 100 can also include the one or more implanted leadless or electrode-lead pulse generators 106 configured to conduct signals to the leadless cardiac pacemaker that trigger left-ventricular pacing.

In some arrangements, the cardiac pacing system 100 can include or be used with pulse generators 106 such as a cardioverter-defibrillator (CRT-D) or a conventional pacemaker (CRT-P). For example, the leadless cardiac pacemaker 102 can be configured for operation as a left-ventricular pacemaker for cardiac resynchronization therapy using a cardioverter-defibrillator (CRT-D) or cardiac resynchronization therapy using an otherwise conventional pacemaker (CRT-P), in response to wireless conducted signals from at least one implanted leadless or electrode-lead pulse generator 106. The wireless conducted signals are conducted pacing and/or cardiac signals.

The cardiac pacing system 100 can be implemented in various arrangements for multiple therapeutic uses. For example, the leadless cardiac pacemaker 102 can be configured for leadless triggered left-ventricular pacing in response to conducted signals selected from signals from a separate implanted pulse generator, signals from one or more electrode-leads of a separate implanted pulse generator, a right-ventricular pacing pulse delivered by an implanted pulse generator, an atrial pacing pulse delivered by an implanted pulse generator, a signal delivered in combination with a cardioversion function, and a signal delivered in combination with a defibrillation function.

In one example application, the leadless cardiac pacemaker 102 can be operative as a "slave" left-ventricular leadless cardiac pacemaker triggered by an atrial pacing pulse or right-ventricular pacing pulse of the pulse generator operative for right-ventricular and/or atrial pacing.

In another example, application, the leadless pacemaker 102 can be configured for left-ventricular pacing triggered by conducted communication from a pulse generator 106 which is implanted within the body. Left-ventricular pacing can be triggered by a right-ventricular pacing pulse or atrial pacing pulse delivered by the pulse generator 106.

The leadless cardiac pacemaker 102 has two or more electrodes 108 abutting or adjacent to a housing 110 and configured for delivering pacing pulses and operative as an incoming communication channel for receiving triggering signals from the pulse generator 106. The triggering information can be an electrical potential difference resulting from a right-ventricular pacing pulse or an atrial pacing pulse of an implanted pulse generator and electrode-lead system.

The illustrative cardiac pacing system 100 further comprises a controller 112 coupled to the electrodes 108 adapted to examine triggering information validity. For a valid condition, the controller 112 can activate delivery of a pacing pulse following a predetermined delay of zero or more milliseconds.

The incoming communication channel can communicate information such as pacing rate, pulse duration, sensing threshold, delay intervals, refractory time intervals, stimulation pulse amplitudes, and parameters commonly programmed from an external programmer in a pacemaker.

The electrodes 108 can also be used as an outgoing communication channel for communicating information such as programmable parameter settings, pacing and sensing event counts, battery voltage, battery current, information commonly displayed by external programmers used with pacemakers, and echoed information from the incoming channel to confirm correct programming.

In one example control technique, the controller 112 can monitor electrical signals on the electrodes 108 and examine the potential difference resulting from a pacing pulse. The controller 112 can also decode information encoded in the pacing pulse and evaluate the decoded information for pacing pulse signature validation.

In another example, the controller 112 can monitor electrical signals on the electrodes 108 and examine output pulse duration from an implanted pulse generator 106 for usage as a signature for determining triggering information validity. For a signature arriving within predetermined limits, the controller 112 can activate delivery of a pacing pulse following a predetermined delay of zero or more milliseconds. The predetermined delay can be determined from information sources such as information preset at manufacture, information that is programmed via an external programmer, and information attained by adaptive monitoring and conformance to duration of a triggering signal.

In another example, the controller 112 can monitor electrical signals on the electrodes 108 and examine information or parameters such as output pulse amplitude, duration, and rate from an implanted pulse generator for usage as a signature for determining triggering information validity. For a signature that arrives within predetermined limits, the controller 112 can activate delivery of a pacing pulse following a predetermined delay of zero or more milliseconds.

In other embodiments, a controller 112 coupled to the two electrodes 108 can also be adapted to trigger delivery of a left-ventricular pacing pulse from an atrial pacing pulse of an implanted pulse generator for cardiac resynchronization therapy (CRT) after a selected atrio-ventricular delay of 50 to 300 milliseconds. The controller 112 can vary the atrio-ventricular delay according to time since a last delivered left-ventricular pacing pulse whereby a shorter atrio-ventricular delay is selected for a higher atrial rate.

Also referring to FIG. 1B, the block diagram illustrates an embodiment of a cardiac pacing system 100 comprising a leadless cardiac pacemaker 102 configured for implantation in electrical contact with a cardiac chamber 104. The pacemaker 102 receives and evaluates triggering information from an implanted pulse generator 106 via an electrical signal conducted from an atrial or ventricular pacing pulse delivered by the implanted pulse generator 106.

The pacing system 100 can further comprise one or more implanted leadless or electrode-lead pulse generators 106 which are configured to conduct signals that trigger left-ventricular pacing to the leadless cardiac pacemaker by direct conduction using modulated signals at a frequency in a range from approximately 10 kHz to 100 kHz.

The leadless cardiac pacemaker 102 can be configured for retriggering by the implanted pulse generator 106 whereby the leadless cardiac pacemaker 102 generates a pacing pulse after a predetermined time with no received triggering signal and the predetermined time is preset slightly longer than a pacing interval of the implanted pulse generator 106, enabling the leadless cardiac pacemaker 102 to operate as a synchronized redundant pacemaker.

The pacemaker 106 can trigger delivery of an atrial pacing pulse in response to sensing of an atrial heartbeat in sinus rhythm and in response to detection of sinus rhythm below a selected rate for atrial demand pacing.

The controller 112 can be adapted to limit synchronous pacing pulse delivery rate to a selected maximum rate.

In some embodiments, multiple leadless cardiac pacemakers 102 can be included in the system 100 and configured for implantation in electrical contact with at least one cardiac chamber 104 and distributed epicardially. The multiple leadless cardiac pacemakers 102 can respond with pacing activity that is timed from an initial triggering pulse for generating simultaneous pulses for defibrillation or cardioversion therapy.

Referring again to FIG. 1B, a schematic block diagram depicts a generic embodiment of a biostimulation system 100 comprising a biostimulator 102 configured for implantation in electrical contact with a biological tissue 104 and configured for receiving and evaluating triggering information from an implanted pulse generator 106 via an electrical signal conducted from an stimulation pulse delivered by the implanted pulse generator.

Again referring to FIG. 1B, the leadless pacemaker 102 has functional elements substantially enclosed in a hermetic housing 110. The pacemaker has at least two electrodes 108 located within, on, or near the housing 110, for delivering pacing pulses to and optionally sensing electrical activity from the muscle of the cardiac chamber, for receiving triggering signals from another pulse generator implanted within the body, and optionally for bi-directional communication with at least one other device within or outside the body. Hermetic feedthroughs 130, 131 conduct electrode signals through the housing 110. The housing 110 contains a primary battery 114 to provide power for pacing, receiving triggering signals, optionally for sensing, and optionally for other communication. It optionally contains circuits 132 for sensing cardiac activity from the electrodes 108; circuits 134 for receiving triggering information and optionally other information from at least one other device via the electrodes 108; and a pulse generator 116 for generating pacing pulses for delivery via the electrodes 108 and also optionally for transmitting information to at least one other device via the electrodes 108. The pacemaker 102 further optionally contains circuits for monitoring device health, for example a battery current monitor 136 and a battery voltage monitor 138. The pacemaker 102 further contains processor or controller circuits 112 for controlling these operations in a predetermined manner.

The incoming communication channel serves to receive triggering information for the leadless cardiac pacemaker. In a most simple expected manner, the triggering information can comprise an electrical potential difference appearing on the electrodes 108 of the leadless cardiac pacemaker 102 resulting from a right-ventricular pacing pulse or an atrial pacing pulse of another pulse generator 106 and electrode-lead system implanted in the body. When the leadless cardiac pacemaker receives the triggering information via electrodes 108 and circuits 134, controlling or processing circuits 112 examine the validity of the triggering information. If the information is determined to be valid, the controller 112 instructs the pulse generator 116 to deliver a pacing pulse, optionally after a predetermined delay.

Information communicated on the incoming communication channel can also optionally include pacing rate, pulse duration, sensing threshold, and other parameters commonly programmed via external intervention as in conventional pacemakers. The information communicated on the optional outgoing communication channel can include programmable parameter settings, event counts such as pacing and sensing counts, battery voltage, battery current, and other information commonly displayed by external programmers used with conventional pacemakers. The outgoing communication channel can also echo information from the incoming channel to confirm correct programming.

Also shown in FIG. 1B, the primary battery 114 has positive terminal 140 and negative terminal 142. A suitable primary battery has an energy density of at least 3 W·h/cc, a power output of 70 microwatts, a volume less than 1 cubic centimeter, and a lifetime greater than 5 years.

One suitable primary battery uses beta-voltaic technology, licensed to BetaBatt Inc. of Houston, Tex., USA, and developed under a trade name DEC™ Cell, in which a silicon wafer captures electrons emitted by a radioactive gas such as tritium. The wafer is etched in a three-dimensional surface to capture more electrons. The battery is sealed in a hermetic package which entirely contains the low-energy particles emitted by tritium, rendering the battery safe for long-term human implant from a radiological-health standpoint. Tritium has a half-life of 12.3 years so that the technology is more than adequate to meet a design goal of a lifetime exceeding 5 years.

Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the processor 112 with an indication of battery current drain and indirectly of device health.

The illustrative power supply can be a primary battery 114 such as a beta-voltaic converter that obtains electrical energy from radioactivity. In some embodiments, the power supply can be selected as a primary battery 114 that has a volume less than approximately 1 cubic centimeter.

In an illustrative embodiment, the primary battery 114 can be selected to source no more than 70 microwatts instantaneously since a higher consumption may cause the voltage across the battery terminals to collapse. Accordingly in one illustrative embodiment the circuits depicted in FIG. 1B can be designed to consume no more than a total of 64 microwatts. The design avoids usage of a large filtering capacitor for the power supply or other accumulators such as a supercapacitor or rechargeable secondary cell to supply peak power exceeding the maximum instantaneous power capability of the battery, components that would add volume and cost.

In various embodiments, the system can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

Implantable systems that communicate via long distance radio-frequency (RF) schemes, for example Medical Implant Communication Service (MICS) transceivers, which exhibit a peak power requirement on the order of 10 milliwatts, and other RF or inductive telemetry schemes are unable to operate without use of an additional accumulator. Moreover, even with the added accumulator, sustained operation would ultimately cause the voltage across the battery to collapse.

Figure 2:
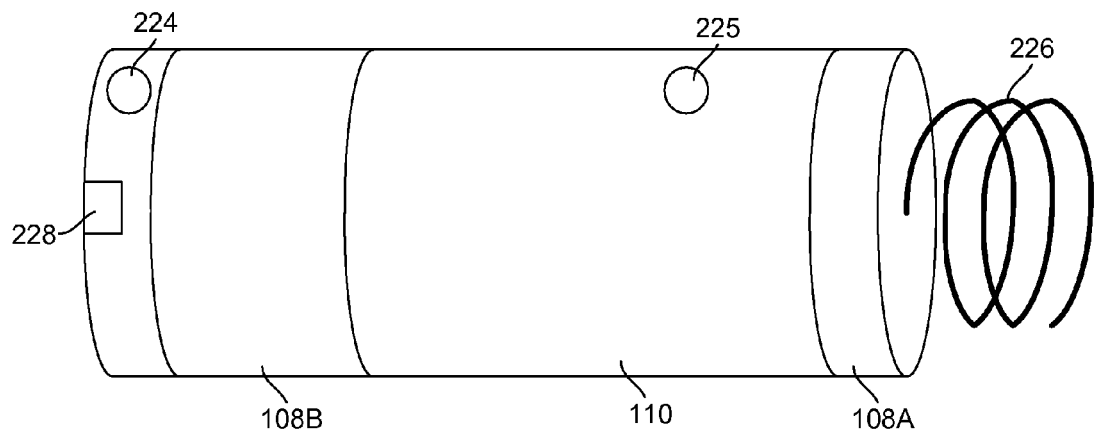
FIG. 2 is a pictorial diagram showing the physical location of some elements of an embodiment of a leadless biostimulator.

Referring to FIG. 2, a schematic pictorial view shows an embodiment of the leadless cardiac pacemaker 102 that can be used in the cardiac pacing system 100. The leadless cardiac pacemaker 102 comprises a hermetic housing 110 configured for placement on or attachment to the inside or outside of a cardiac chamber 104. Two or more electrodes 108 abut or are adjacent to the housing 110. The electrodes 108 are configured for delivering pacing pulses and receiving triggering signals from the pulse generator 106. The electrodes 108 can also sense electrical activity from cardiac chamber muscle.

Furthermore, the electrodes 108 are adapted for bi-directional communication with at least one other device within or outside the body. For example, the leadless pacemaker 102 can be configured to communicate with a non-implanted programmer or one or more implanted pulse generators via the same electrodes 108 that are used for delivering pacing pulses. The illustrative leadless pacemaker 102 is adapted for antenna-less and telemetry coil-less communication. Usage of the electrodes 108 for communication enables the leadless pacemaker 102 to communicate with a non-implanted programmer or one or more implanted pulse generators via communication that adds nothing to power requirements in addition to power requirements for cardiac pacing.

The illustrative example avoids usage of radiofrequency (RF) communication to send pacing instructions to remote electrodes on a beat-to-beat basis to cause the remote electrodes to emit a pacing pulse. RF communication involves use of an antenna and modulation/demodulation unit in the remote electrode, which increase implant size significantly. Also, communication of pacing instructions on a beat-to-beat basis increases power requirements for the main body and the remote electrode. In contrast, the illustrative system and stimulator do not require beat-to-beat communication with any controlling main body.

The illustrative leadless pacemaker 102 includes an internal power source that can supply all energy for operations and pulse generation. In contrast, some conventional implanted pulse generators have remote pacing electrodes that receive some or all energy from an energy source through an RF induction technique, an energy transfer scheme that employs a large loop antenna on the remote electrode which increases size significantly. In addition, energy transfer with the RF induction technique is inefficient and is associated with a significant increase in battery size of the energy source. In contrast, the illustrative leadless pacemaker 102 uses an internal battery and does not require energy to be drawn from outside sources. Also in the conventional system, the energy source receives sensing information by RF communication from the remote electrodes and sends pacing instructions to the electrodes on a beat-to-beat basis in a configuration that uses an addressing scheme in which the identity of specific remote pacing electrodes is stored in the energy source memory. The conventional method can also be inefficient due to overhead for transmitting an identification number from/to a generic pacing electrode at implant and/or during sensing. The illustrative leadless pacemaker 102 avoids such overhead through a structure in which pulse generation functionality is independent within a single implantable body.

Another conventional technology uses a system of addressable remote electrodes that stimulate body tissue without requiring a main body to send commands for individual stimulations. The remote electrodes are specified to be of a size and shape suitable for injection rather than for endocardial implantation. A controller sets operating parameters and sends the parameters to remote electrodes by addressable communication, enabling the remote electrodes function relatively autonomously while incurring some overhead to controller operations. However, the remote electrodes do not sense or monitor cardiac information and rely on the main body to provide sensing functionality. In contrast, the illustrative leadless pacemaker 102 combines pacing and sensing of intrinsic cardiac activity in a single implantable body.

The illustrative leadless pacemaker 102 has one or more structures that enable fixture to tissue, for example suture holes 224, 225 or a helix 226. The affixing structures enable implantation of the leadless pacemaker 102 adjacent to an inside or outside wall of a cardiac chamber 104, further enabling leadless conductive communication with the pulse generator 106.

Also shown in FIG. 2, a cylindrical hermetic housing 110 is shown with annular electrodes 108 at housing extremities. In the illustrative embodiment, the housing 110 can be composed of alumina ceramic which provides insulation between the electrodes. The electrodes 108 are deposited on the ceramic, and are platinum or platinum-iridium.

Several techniques and structures can be used for attaching the housing 110 to the interior or exterior wall of cardiac muscle 104.

A helix 226 and slot 228 enable insertion of the device endocardially or epicardially through a guiding catheter. A screwdriver stylet can be used to rotate the housing 110 and force the helix 226 into muscle 104, thus affixing the electrode 108A in contact with stimulable tissue. Electrode 108B serves as an indifferent electrode for sensing and pacing. The helix 226 may be coated for electrical insulation, and a steroid-eluting matrix may be included near the helix to minimize fibrotic reaction, as is known in conventional pacing electrode-leads.

In other configurations, suture holes 224 and 225 can be used to affix the device directly to cardiac muscle with ligatures, during procedures where the exterior surface of the heart is exposed.

Other attachment structures used with conventional cardiac electrode-leads including tines or barbs for grasping trabeculae in the interior of the ventricle, atrium, or coronary sinus may also be used in conjunction with or instead of the illustrative attachment structures.

Figure 3:
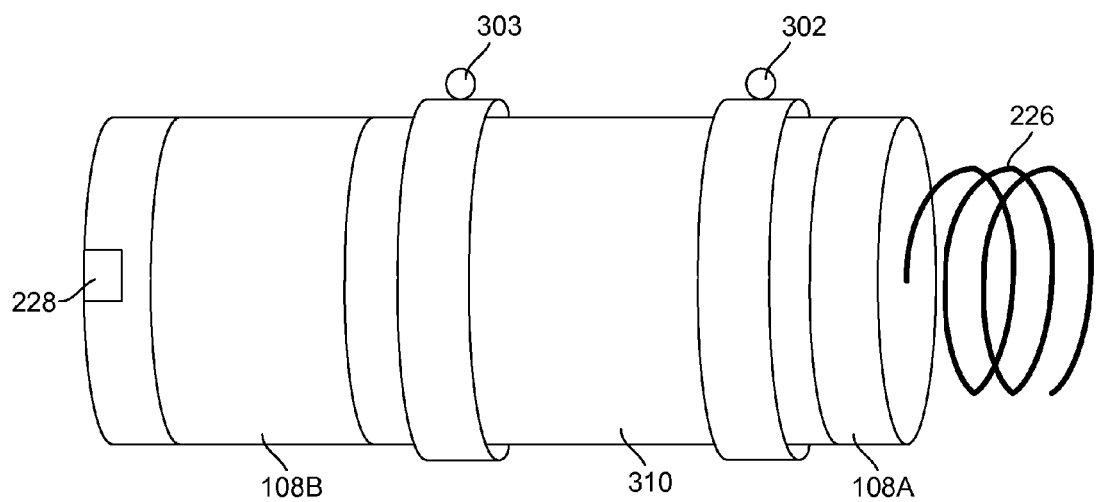
FIG. 3 is a pictorial diagram that depicts the physical location of some elements in an alternative embodiment of a leadless biostimulator.

Referring to FIG. 3, a pictorial view shows another embodiment of a pulse generator that includes a cylindrical metal housing 310 with an annular electrode 108A and a second electrode 108B. Housing 310 can be constructed from titanium or stainless steel. Electrode 108A can be constructed using a platinum or platinum-iridium wire and a ceramic or glass feed-thru to provide electrical isolation from the metal housing. The housing can be coated with a biocompatible polymer such as medical grade silicone or polyurethane except for the region outlined by electrode 108B. The distance between electrodes 108A and 108B should be approximately 1 cm to optimize sensing amplitudes and pacing thresholds. A helix 226 and slot 228 can be used for insertion of the device endocardially or epicardially through a guiding catheter. In addition, suture sleeves 302 and 303 made from silicone can be used to affix to the device directly to cardiac muscle with ligatures.

Figure 4:
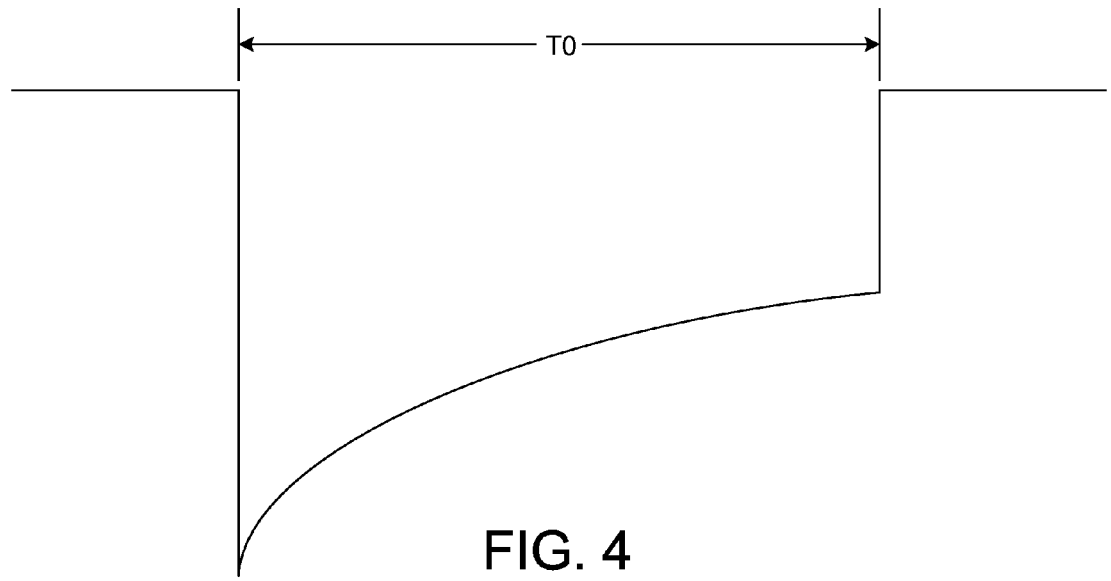
FIG. 4 is a time waveform graph illustrating a conventional pacing pulse.

Referring to FIG. 4, a typical output-pulse waveform for a conventional pacemaker is shown. The approximately-exponential decay is due to discharge of a capacitor in the pacemaker through the approximately-resistive load presented by the electrodes and leads. Typically the generator output is capacitor-coupled to one electrode to ensure net charge balance. The pulse duration is shown as T0 and is typically 500 microseconds.

The illustrative leadless pulse generator 102 as shown in FIGS. 1, 2, and 3 can use the duration T0 of the output pulse of another pulse generator 106 implanted within the body as a "signature" to aid the processor 112 in determining the validity of triggering information received via electrodes 108 and receiving circuits 134. When such a signature arrives with duration within predetermined limits, processor 112 recognizes the signature as a valid triggering signal, and instructs pulse generator 116 to generate a pacing pulse, optionally after a delay.

The predetermined limits for evaluating duration of the received triggering information can be stored in the depicted leadless pulse generator 102 in various manners. For example, limits can be preset at manufacture, programmed using a programmer outside the body, or can be "learned" by the leadless pulse generator 102. For example, if the leadless pulse generator 102 detects a predetermined number of pulses via electrodes 108, and receiving circuits 134, each of such pulses with substantially the same duration, such as within 10 microseconds between pulses, and each is separated from the others by an interval characteristic of cardiac pacing, such as 400 to 1200 milliseconds, then the leadless pulse generator can use the maximum and minimum measured durations to establish limits for validity of received triggering signals.

In addition, the leadless pacemaker 102 can use the amplitude of the output pulse of another pulse generator to validate the pacing pulse, since pacing amplitudes tend to be higher magnitude than other electrical signals in the body.

In the illustrative leadless pacemaker 102, the other triggering pulse generator 106 implanted in the body generates a pacing pulse to trigger each pacing pulse generated by the leadless pacemaker 102. In a simple embodiment, the other triggering pulse generator 106 provides right ventricular pacing pulses as needed, and the left-ventricular leadless pulse pacemaker 102 generates a triggered pacing pulse to the left ventricle substantially synchronously with the detected right-ventricular pacing pulse, or after a predetermined delay. The predetermined delay can be a few tens of milliseconds typically and can be programmed from a programmer outside the body or communicated from the other pulse generator 106 implanted within the body.

Conditions can be sufficient or even advantageous in certain applications of CRT to pace the left ventricle a few tens of milliseconds before pacing the right ventricle, or to dispense altogether with right-ventricular pacing and provide only left-ventricular pacing. The leadless pacemaker 102 can use triggering information from the atrial pacing pulse of the other pulse generator 106 implanted within the body to provide CRT by delaying the left-ventricular pacing pulse typically by 50 to 300 milliseconds from the received atrial pacing pulse. The leadless pacemaker 102 can vary the atrio-ventricular delay according to the time since the last delivered left-ventricular pacing pulse, in general providing shorter atrio-ventricular delays for higher atrial rates. To realize the illustrative operation, the other pulse generator 106 implanted within the body provides triggered atrial pacing, defined as delivery of an atrial pacing pulse after sensing an atrial heartbeat in sinus rhythm, or when sinus rhythm falls below a predetermined rate and the atrial pacemaker paces the atrium on demand.

When the depicted leadless pacemaker 102 is providing a pacing pulse but is not optionally sending data for communication, the pacing waveform of the leadless pacemaker 102 can also resemble the conventional pacing pulse shown in FIG. 4, although of course the pulse duration can differ from that of the other pulse generator 106 implanted within the body.

Figure 5:
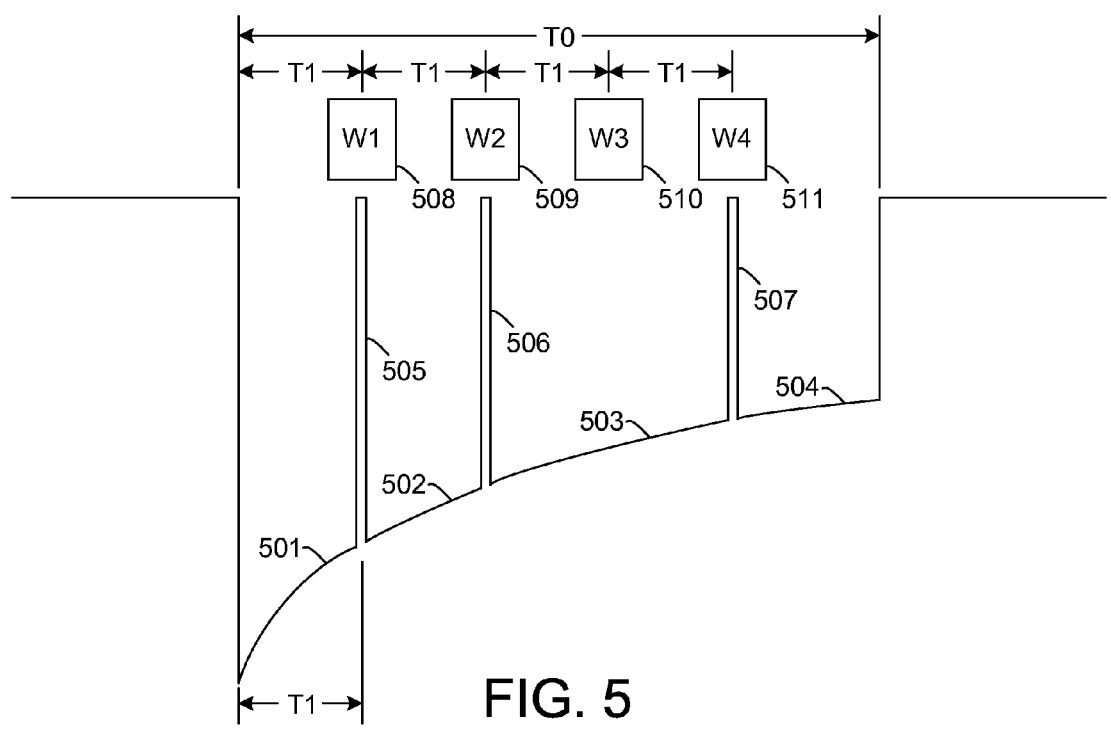
FIG. 5 is a time waveform graph depicting a pacing pulse adapted for communication as implemented for an embodiment of the illustrative pacing system.

Referring to FIG. 5, a time waveform graph depicts an embodiment of an output-pacing pulse waveform adapted for communication. The output-pulse waveform of the illustrative leadless pacemaker 102 is shown during a time when the pacemaker 102 is optionally sending data for communication and also delivering a pacing pulse, using the same pulse generator 116 and electrodes 108 for both functions.

FIG. 5 shows that the pulse generator 102 has divided the output pulse into shorter pulses 501, 502, 503, 504; separated by notches 505, 506, and 507. The pulse generator 102 times the notches 505, 506, and 507 to fall in timing windows W1, W2, and W4 designated 508, 509, and 511 respectively. Note that the pacemaker 102 does not form a notch in timing window W3 designated 510. The timing windows are each shown separated by a time T1, approximately 100 microseconds in the example.

As controlled by processor 112, pulse generator 116 selectively generates or does not generate a notch in each timing window 508, 509, 510, and 511 so that the device 102 encodes four bits of information in the pacing pulse. A similar scheme with more timing windows can send more or fewer bits per pacing pulse. The width of the notches is small, for example approximately 15 microseconds, so that the delivered charge and overall pulse width, specifically the sum of the widths of the shorter pulses, in the pacing pulse is substantially unchanged from that shown in FIG. 4. Accordingly, the pulse shown in FIG. 5 can have approximately the same pacing effectiveness as that shown in FIG. 4, according to the law of Lapique which is well known in the art of electrical stimulation.

In a leadless cardiac pacemaker, a technique can be used to conserve power when detecting information carried on pacing pulses from other implanted devices. The leadless cardiac pacemaker can have a receiving amplifier that implements multiple gain settings and uses a low-gain setting for normal operation. The low-gain setting could be insufficiently sensitive to decode gated information on a pacing pulse accurately but could detect whether the pacing pulse is present. If an edge of a pacing pulse is detected during low-gain operation, the amplifier can be switched quickly to the high-gain setting, enabling the detailed encoded data to be detected and decoded accurately. Once the pacing pulse has ended, the receiving amplifier can be set back to the low-gain setting. For usage in the decoding operation, the receiving amplifier is configured to shift to the more accurate high-gain setting quickly when activated. Encoded data can be placed at the end of the pacing pulse to allow a maximum amount of time to invoke the high-gain setting.

Figure 6:
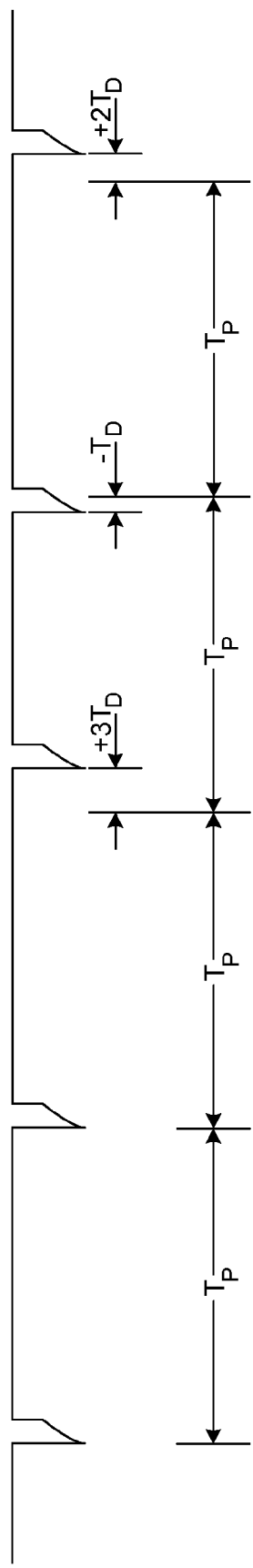
FIG. 6 is a time waveform graph depicting a pacing pulse adapted for communication using off-time variation as implemented for an embodiment of the illustrative pacing system.

Alternatively or in addition to the use of notches in the stimulation pulse for encoding and transmitting information, the pulses can have varying off-times, for instance times between pulses during which no stimulation occurs. Varying off-times can be small, for example less than 10 milliseconds total or any suitable duration, and can impart information based on the difference between a specific pulse's off-time and a preprogrammed off-time based on desired heart rate. For example, the device could impart four bits of information with each pulse by defining 16 off-times centered around the preprogrammed off-time. FIG. 6 is a graph that shows an example embodiment of a sample pulse generator output which incorporates the varying off-time scheme. Time $T_P$ represents the preprogrammed pulse timing. Time $T_d$ is a delta time associated with a single bit resolution for the data sent by the pulse generator. The number of $T_d$ time increments before or after the moment specified by $T_P$ gives the specific data element transmitted. The receiver of the pulse generator's communication has information relating to the pulse timing $T_P$ in advance. The communication scheme is most useful in applications of overdrive pacing in which pulse timing $T_P$ is not changing or altered by detected beats.

FIG. 5 depicts a technique in which information is encoded in notches in the pacing pulse. FIG. 6 shows a technique of conveying information by modulating the off-time between pacing pulses. Alternatively or in addition to the two illustrative coding schemes, overall pacing pulse width can be used to impart information. For example, a paced atrial beat may exhibit a pulse width of 500 microseconds and an intrinsic atrial contraction can be identified by reducing the pulse width by 30 microseconds. Information can be encoded by the absolute pacing pulse width or relative shift in pulse width. Variations in pacing pulse width can be relatively small and have no impact on pacing effectiveness.

The illustrative scheme for transmitting data does not significantly increase the current consumption of the pacemaker. For example, the pacemaker could transmit data continuously in a loop, with no consumption penalty.

As described hereinbefore, the leadless pulse generator 102 can evaluate information received on the incoming channel to determine validity for triggering pacing pulses. The coding scheme illustrated in FIG. 5 can be used to provide a more distinctive signature for the other implanted pulse generator 106. In the depicted embodiment, the other implanted pulse generator 106 encodes an output pulse in the manner illustrated in FIG. 5 and the leadless pulse generator 102 uses the additional data encoded in the manner shown in FIG. 5 to evaluate the received information to determine whether or not the pulse corresponds to the atrial or ventricular pacing pulse of the other implanted pulse generator 106.

To ensure the leadless cardiac pacemaker functions correctly, a specific minimum internal supply voltage is maintained. When pacing tank capacitor charging occurs, the supply voltage can drop from a pre-charging level which can become more significant when the battery nears an end-of-life condition and has reduced current sourcing capability. Therefore, a leadless cardiac pacemaker can be constructed with a capability to stop charging the pacing tank capacitor when the supply voltage drops below a specified level. When charging ceases, the supply voltage returns to the value prior to the beginning of tank capacitor charging.

In another technique, the charge current can be lowered to prevent the supply voltage from dropping below the specified level. However, lowering the charge current can create difficulty in ensuring pacing rate or pacing pulse amplitude are maintained, since the lower charge current can extend the time for the pacing tank capacitor to reach a target voltage level.

Referring again to FIG. 1B, the circuit 132 for receiving communication via electrodes 108 receives the triggering information as described and can also optionally receive other communication information, either from the other implanted pulse generator 106 or from a programmer outside the body. This other communication could be coded with a pulse-position scheme as described in FIG. 5 or could otherwise be a pulse-modulated or frequency-modulated carrier signal, preferably from 10 kHz to 100 kHz.

The illustrative leadless pacemaker 102 could otherwise receive triggering information from the other pulse generator 106 implanted within the body via a pulse-modulated or frequency-modulated carrier signal, instead of via the pacing pulses of the other pulse generator 106.

As in conventional pacemakers, the leadless pacemaker 102 can include in controller 112 a capability to limit the rate of delivering synchronous pacing pulses, typically to 150 pulses per minute or less. An independent hardware rate limiter can also be used to prevent rapid pacing in case of hardware or software failure, as in conventional pacemakers.

In the CRT application described herein, the leadless cardiac pacemaker 102 can provide left-ventricular pacing for amelioration of heart failure but typically does not provide beat-to-beat life support, as with a conventional pacemaker or implantable cardioverter-defibrillator. Consequently certain functions considered essential in a conventional cardiac pacemaker can be optional in the illustrative application. Features such as sensing cardiac activity, communication from or to an external programmer, and monitoring device health, while potentially beneficial, are not essential to the operation of the pacemaker 102.

In an example of a configuration for a cardiac pacing system 102, multiple leadless pacemakers 102 can be distributed around the heart epicardially, endocardially, or in a combination of epicardially and endocardially, and operate in a coordinated manner based on timing from an initial triggering pulse to generate pulses simultaneously, thereby providing defibrillation or cardioversion therapy.

A slight modification of a stored program in processor 112 enables the leadless cardiac pacemaker 102 to be retriggered rather than triggered by a pacing pulse from another pulse generator 106 implanted in the body so that the leadless cardiac pacemaker 102 generates a pacing pulse after a predetermined time with no received triggering signal. The predetermined time can be preset slightly longer than the pacing interval of the other implanted pulse generator 106 so that the leadless pulse generator 102 serves as a synchronized redundant pacemaker. Synchronized redundant pacing is useful in pacemaker-dependent patients to ensure continued pacing in the event of failure of one implanted pulse generator. Use of two such leadless triggered cardiac pacemakers, one with a slightly longer retriggering interval than the other, would ensure continued pacing if either device fails.

Referring again to FIG. 1A, in accordance with another embodiment a cardiac pacing system 100 comprises a leadless cardiac pacemaker 102 that is configured for implantation in electrical contact with a cardiac chamber 104 and configured for delivering a pacing pulse and encoding outgoing communication in the pacing pulse whereby a power requirement for the outgoing communication adds nothing above the power requirement for delivering the pacing pulse.

In a specific embodiment, the outgoing communication power requirement does not exceed approximately 25 microwatts.

In another particular embodiment of a cardiac pacing system 100, a leadless cardiac pacemaker 102 can be configured for implantation in electrical contact with a left ventricular cardiac chamber and configured for leadless triggered left-ventricular pacing in response to conducted signals from a pulse generator 106 and powered by a battery 114 contained within a volume of less than one cubic centimeter.

With regard to operating power requirements in the leadless cardiac pacemaker 102, for purposes of analysis, a pacing pulse of 5 volts and 5 milliamps amplitude with duration of 500 microseconds and a period of 500 milliseconds has a power requirement of 25 microwatts.

In an example embodiment of the leadless pacemaker 102, the processor 112 typically includes a timer with a slow clock that times a period of approximately 10 milliseconds and an instruction-execution clock that times a period of approximately 1 microsecond. The processor 112 typically operates the instruction-execution clock only briefly in response to events originating with the timer, communication amplifier 134, or cardiac sensing amplifier 132. At other times, only the slow clock and timer operate so that the power requirement of the processor 112 is no more than 5 microwatts.

For a pacemaker that operates with the aforementioned slow clock, the instantaneous power consumption specification, even for a commercially-available micropower microprocessor, would exceed the battery's power capabilities and would require an additional filter capacitor across the battery to prevent a drop of battery voltage below the voltage necessary to operate the circuit. The filter capacitor would add avoidable cost, volume, and potentially lower reliability.

For example, a microprocessor consuming only 100 microamps would require a filter capacitor of 5 microfarads to maintain a voltage drop of less than 0.1 volt, even if the processor operates for only 5 milliseconds. To avoid the necessity for such a filter capacitor, an illustrative embodiment of a processor can operate from a lower frequency clock to avoid the high instantaneous power consumption, or the processor can be implemented using dedicated hardware state machines to supply a lower instantaneous peak power specification.

In a pacemaker, the cardiac sensing amplifier typically operates with no more than 5 microwatts. A communication amplifier at 100 kHz operates with no more than 25 microwatts. The battery ammeter and battery voltmeter operate with no more than 1 microwatt each.

A pulse generator typically includes an independent rate limiter with a power consumption of no more than 2 microwatts.

The total power consumption of the pacemaker is thus 64 microwatts, less than the disclosed 70-microwatt battery output.

Improvement attained by the illustrative cardiac pacing system 100 and leadless cardiac pacemaker 102 is apparent.

The illustrative cardiac pacing system 100 enables left-ventricular pacing for cardiac resynchronization therapy, employing a leadless triggered pacemaker 102 for the left ventricle, in conjunction with another implanted pulse generator 106 with at least one electrode-lead or leadless pulse generator.

The depicted leadless cardiac pacemaker 102 can receive and evaluate triggering information from another implanted pulse generator 106 via an electrical signal conducted from the other pulse generator's atrial or ventricular pacing pulse.

The illustrative cardiac pacing system 100 enables encoding optional outgoing communication in the pacing pulse, so that the total power consumption for outgoing communication and pacing does not exceed the power consumption for pacing alone. Thus, power consumption for outgoing communication is effectively zero because outgoing communication uses the same power already used to create a pacing pulse.

The illustrative leadless cardiac pacemaker 102 can have sensing and processing circuitry that consumes no more than 25 microwatts as in conventional pacemakers.

The described leadless cardiac pacemaker 102 can have an incoming communication amplifier for receiving triggering signals and optionally other communication which consumes no more than 25 microwatts.

Furthermore, the leadless cardiac pacemaker 102 can have a primary battery that exhibits an energy density of at least 3 watt-hours per cubic centimeter (W·h/cc).

Figure 7A:
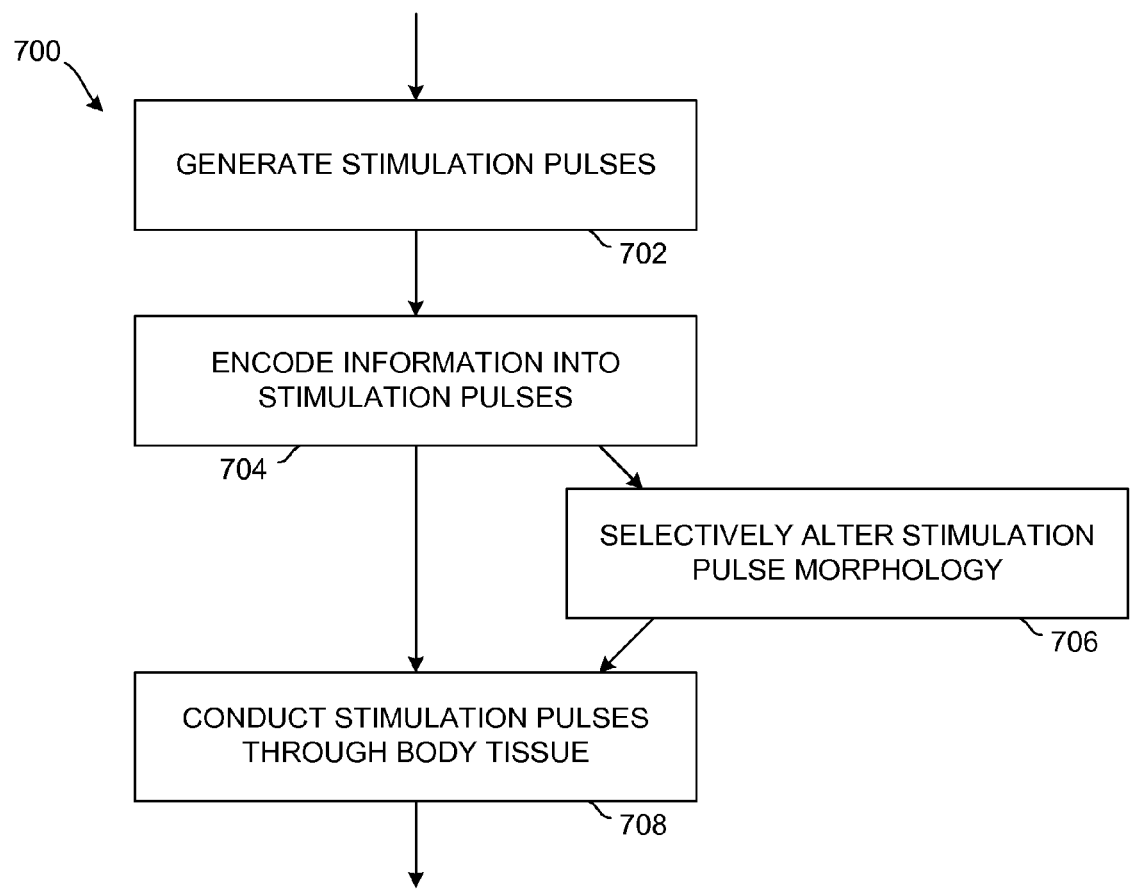
FIGS. 7A through 7D are schematic flow charts depicting an embodiments of a method for communicating in an implantable device.

Referring to FIG. 7A in combination with FIG. 5, a schematic flow chart depicts an embodiment of a method 700 for communicating in an implantable device. Stimulation pulses are generated 702 by an implanted biostimulator. Information can be encoded 704 onto the generated stimulation pulses by the implanted biostimulator by selective alteration 706 of stimulation pulse morphology that is benign to therapeutic effect and energy cost of the stimulation pulse. The stimulation pulses are conducted 708 through body tissue via electrodes for antenna-less and telemetry coil-less communication.

Figure 7B:
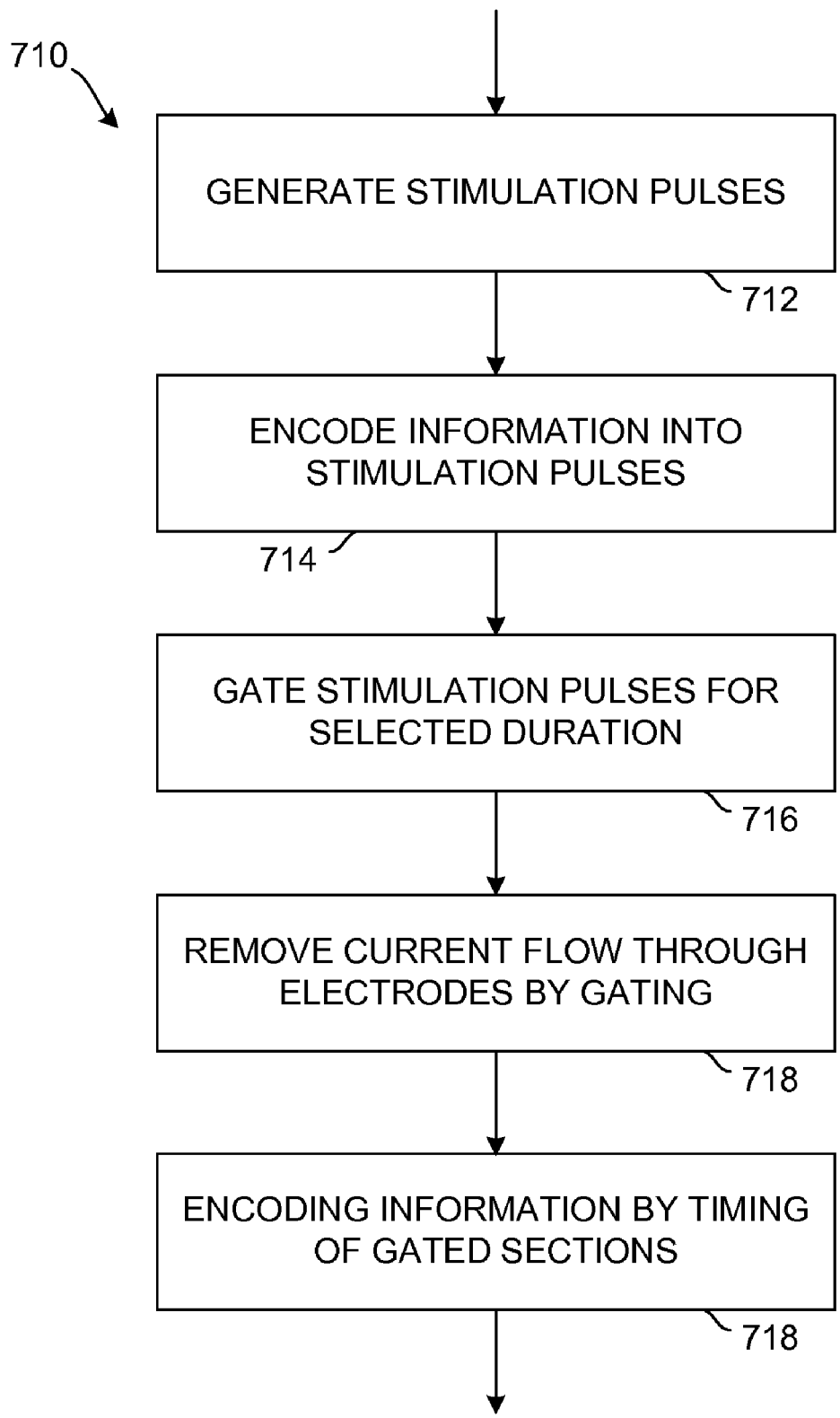

Referring to FIG. 7B, a flow chart depicts operations of another embodiment of a method 710 for communicating in an implantable device. Stimulation pulses are generated 712 on stimulating electrodes of an implanted biostimulator. Information can be encoded 714 onto generated stimulation pulses by gating 716 the stimulation pulses for selected durations at selected timed sections in the stimulation pulses whereby gating removes 718 current flow through the stimulating electrodes and timing of the gated sections encodes 719 the information.

Figure 7C:
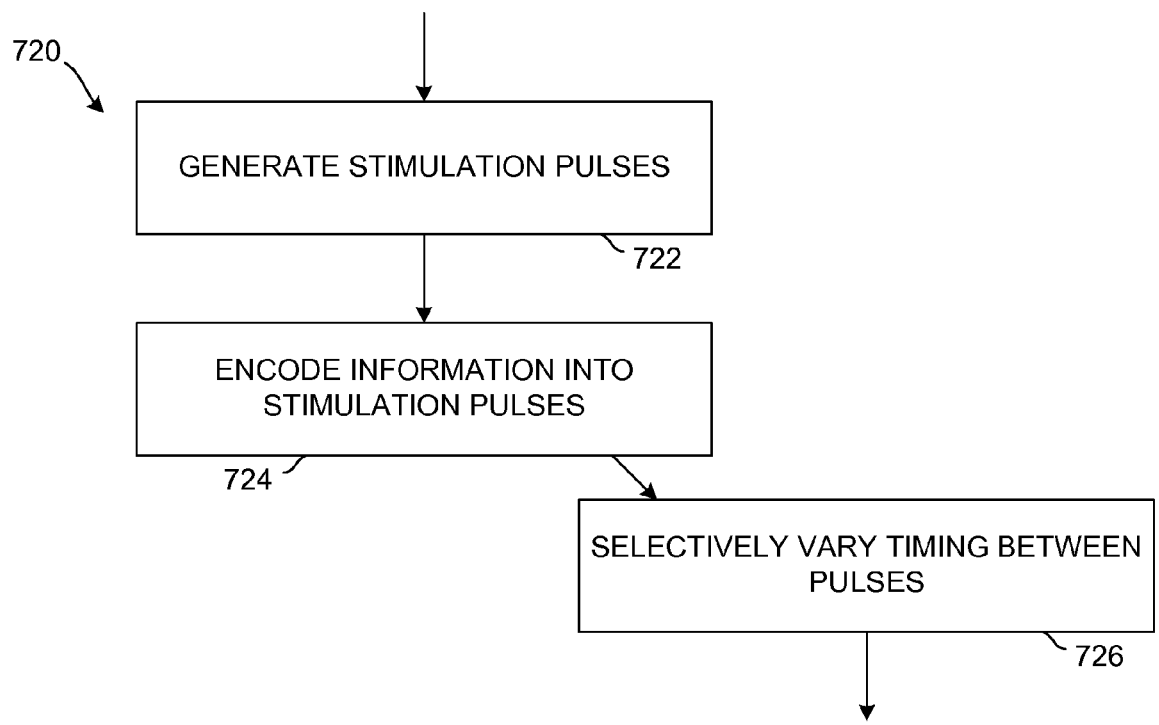

Referring to FIG. 7C, a flow chart depicts an embodiment of a communication method 720 for usage in an implantable device. Stimulation pulses are generated 722 on stimulating electrodes of an implanted biostimulator. Information is encoded 724 onto generated stimulation pulses by selectively varying 726 timing between consecutive stimulation pulses.

Figure 7D:
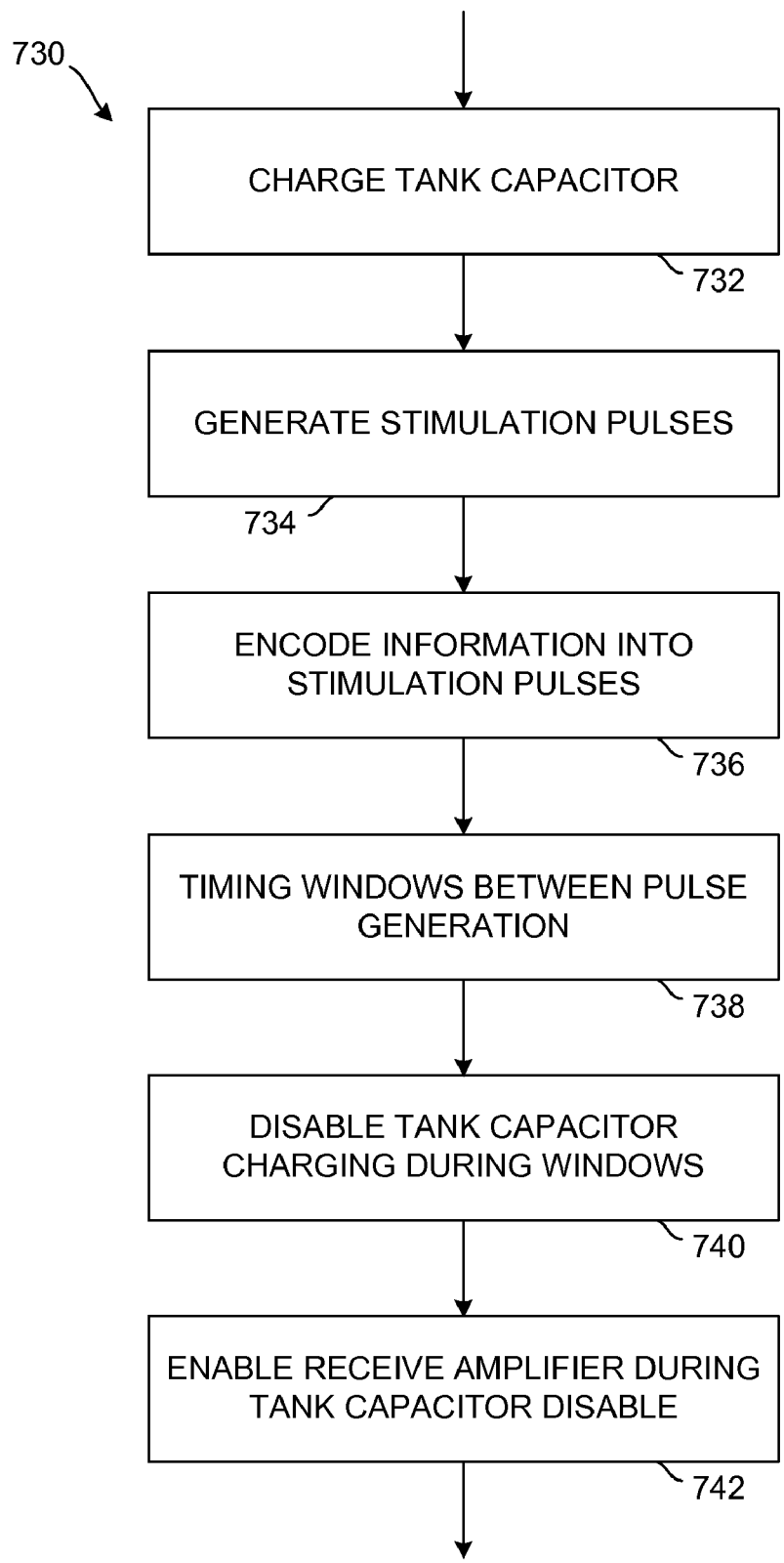

Referring to FIG. 7D, a flow chart depicts another embodiment of a communication method 730 for usage in an implantable device. A tank capacitor is charged 732 in preparation for stimulation pulse generation and stimulation pulses are generated 734 on stimulating electrodes of an implanted biostimulator. Information is encoded 736 onto generated stimulation pulses one or more windows timed 738 between pulse generation. Charging of the tank capacitor can be disabled 740 during the one or more timed windows with a receive amplifier enabled 742 in the implanted biostimulator while the tank capacitor is disabled so that operation of the communications amplifier and charging of the pacing tank capacitor are made mutually exclusive.

In conventional implantable devices, a communication amplifier and a sensing amplifier both continuously consume power, for example constantly requiring on the order of 25 microwatts and 5 microwatts respectively from the battery. In some embodiments of the implantable cardiac pacemaker described herein, operation of the communications amplifier and charging of the pacing tank capacitor can be made mutually exclusive. For example, after the pacing pulse, charging of the pacing tank capacitor can be suspended by an appropriate time window, for example 10 milliseconds. During the window, the communication amplifier can be enabled and ready to receive commands and information from an external programmer or another implantable device. Thus, the 25 microwatts used by the communications amplifier is mutually exclusive from the 25 microwatts consumed by charging the pacing tank capacitor, enabling the total power consumption of the pacemaker to drop to 39 microwatts.

Figure 8A:
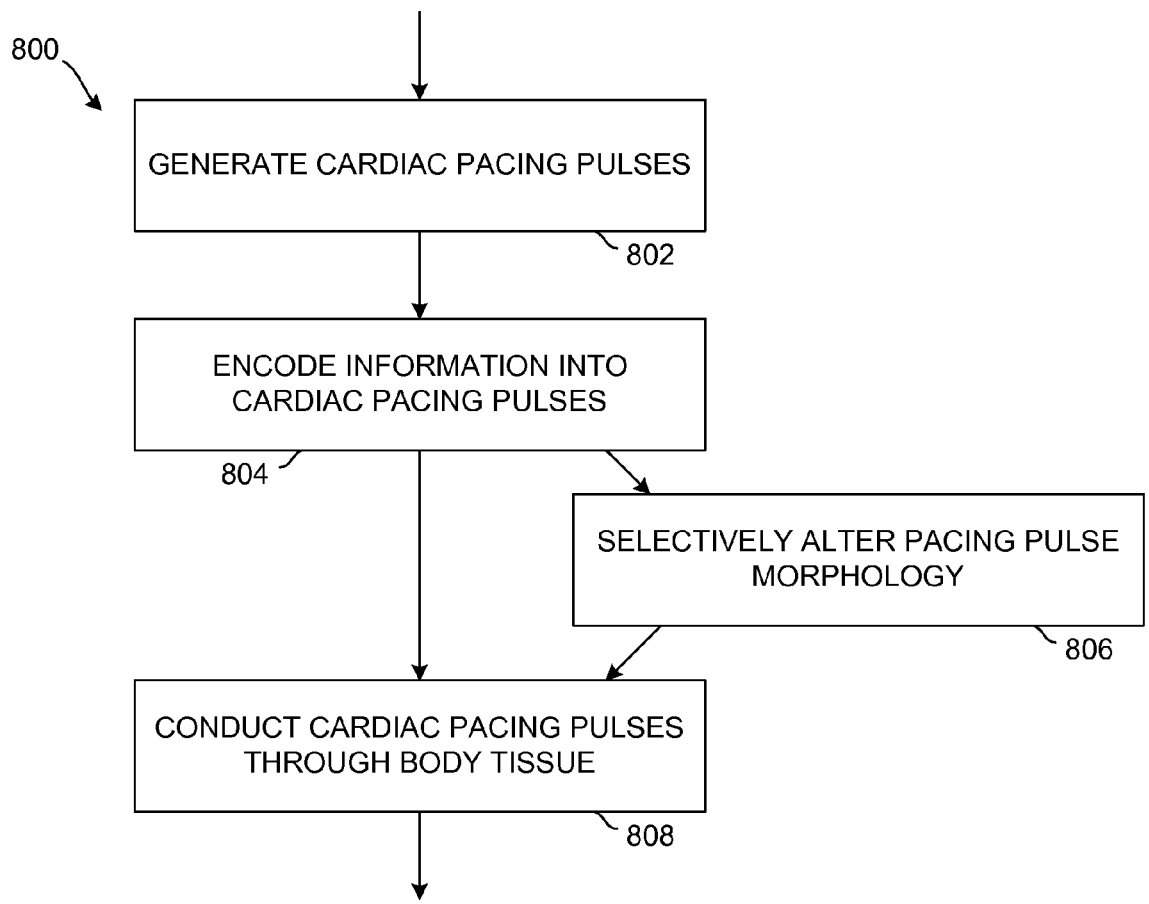
FIGS. 8A and 8B are schematic flow charts showing another embodiment of a method for communicating in a cardiac pacing system.

Referring to FIG. 8A in combination with FIG. 5, a schematic flow chart depicts an embodiment of a method 800 for communicating in a cardiac pacing system. Cardiac pacing pulses are generated 802 by an implanted leadless cardiac pacemaker. Information can be encoded 804 onto the generated cardiac pacing pulses by the implanted leadless cardiac pacemaker by selective alteration 806 of pacing pulse morphology that is benign to therapeutic effect and energy cost of the pacing pulse. The cardiac pacing pulses are conducted 808 into body tissue via electrodes for antenna-less and telemetry coil-less communication.

In some embodiments, the information that is encoded onto generated cardiac pacing pulses at the implanted leadless cardiac pacemaker comprises pacemaker state information, battery voltage, lead impedance, sensed electrocardiogram amplitude, pacemaker current drain, and programmed parameters.

Figure 8B:
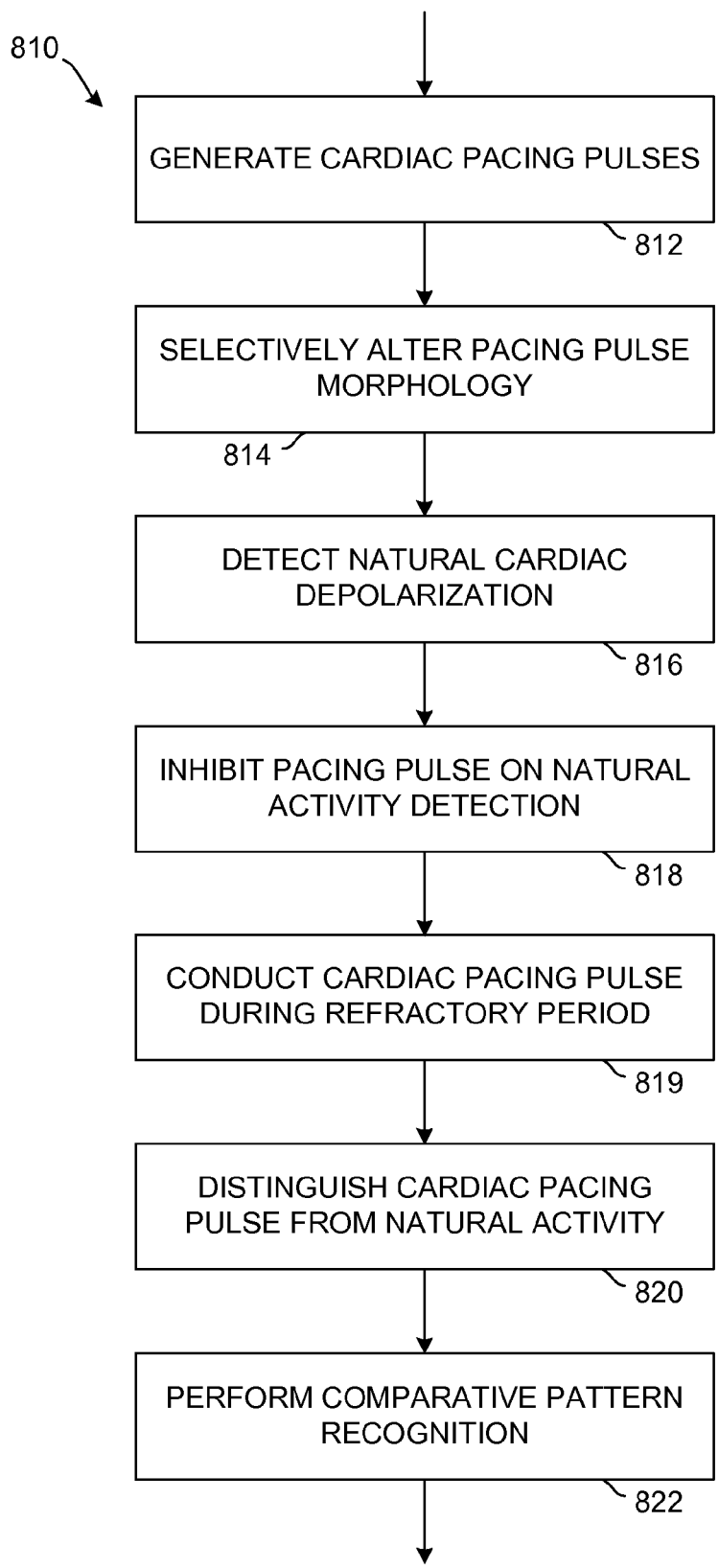

FIG. 8B illustrates an embodiment of the method 810 wherein information is encoded 812 onto generated cardiac pacing pulses at the implanted leadless cardiac pacemaker by selective alteration 814 of pacing pulse morphology that is benign to therapeutic effect and energy cost of the pacing pulse. The implanted leadless cardiac pacemaker detects 816 a natural cardiac depolarization and inhibits 818 cardiac pacing pulse delivery with delay for delivery during a refractory period following the natural cardiac depolarization before conducting 819 the cardiac pacing pulses into body tissue via electrodes for antenna-less and telemetry coil-less communication.

In some embodiments, a generated cardiac pacing pulse is distinguished 820 from a natural cardiac depolarization in an electrocardiogram by comparative pattern recognition 822 of a pacing pulse and an R-wave produced during a cardiac cycle.

Terms "substantially", "essentially", or "approximately", that may be used herein, relate to an industry-accepted tolerance to the corresponding term. Such an industry-accepted tolerance ranges from less than one percent to twenty percent and corresponds to, but is not limited to, component values, integrated circuit process variations, temperature variations, rise and fall times, and/or thermal noise. The term "coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. Inferred coupling, for example where one element is coupled to another element by inference, includes direct and indirect coupling between two elements in the same manner as "coupled".

While the present disclosure describes various embodiments, these embodiments are to be understood as illustrative and do not limit the claim scope. Many variations, modifications, additions and improvements of the described embodiments are possible. For example, those having ordinary skill in the art will readily implement the steps necessary to provide the structures and methods disclosed herein, and will understand that the process parameters, materials, and dimensions are given by way of example only. The parameters, materials, and dimensions can be varied to achieve the desired structure as well as modifications, which are within the scope of the claims. Variations and modifications of the embodiments disclosed herein may also be made while remaining within the scope of the following claims. For example, although the description has some focus on CRT, the pacemaker, system, structures, and techniques can otherwise be applicable to other uses, for example multi-site pacing for prevention of tachycardias in the atria or ventricles. Phraseology and terminology employed herein are for the purpose of the description and should not be regarded as limiting. With respect to the description, optimum dimensional relationships for the component parts are to include variations in size, materials, shape, form, function and manner of operation, assembly and use that are deemed readily apparent and obvious to one of ordinary skill in the art and all equivalent relationships to those illustrated in the drawings and described in the specification are intended to be encompassed by the present description. Therefore, the foregoing is considered as illustrative only of the principles of structure and operation. Numerous modifications and changes will readily occur to those of ordinary skill in the art whereby the scope is not limited to the exact construction and operation shown and described, and accordingly, all suitable modifications and equivalents may be included.

What is claimed is:

1. A cardiac pacing system comprising:
   a leadless cardiac pacemaker configured for implantation in electrical contact with a left ventricular cardiac chamber and performing leadless triggered left-ventricular pacing for cardiac resynchronization therapy (CRT) in response to conducted signals from a co-implanted pulse generator, the leadless cardiac pacemaker comprising a pacing pulse generator configured to generate pulses adapted to perform cardiac pacing and pulses encoding information for transmission as communication signals during a refractory period, the leadless cardiac pacemaker configured to receive communication directly from a non-implanted programmer.

2. The system according to claim 1 further comprising:
   at least one implanted leadless or electrode-lead pulse generator comprising the co-implanted pulse generator, the co-implanted pulse generator being configured to generate pulses adapted to perform cardiac pacing and pulses adapted to encode information for transmission as communication signals to the leadless cardiac pacemaker.

3. The system according to claim 1 wherein the leadless cardiac pacemaker is configured for operation as a left-ventricular pacemaker for cardiac resynchronization therapy in response to wireless conducted signals from the co-implanted pulse generator, the wireless conducted signals being conducted pacing pulse, refractory and/or subliminal signals delivered in response to cardiac contractions, the leadless cardiac pacemaker programmable for operation as the left-ventricular pacemaker by bidirectional communication with a non-implanted programmer wherein information comprising programmable parameter settings is encoded in pulses generated by the pacing pulse generator.

4. The system according to claim 1 wherein the leadless cardiac pacemaker further comprises:
   a hermetic housing configured for placement on or attachment to the inside or outside of a cardiac chamber; and
   at least two electrodes abutting or adjacent to the housing and configured for delivering the pulses from the pacing pulse generator and for receiving triggering signals from the co-implanted pulse generator.

5. The system according to claim 4 wherein the at least two electrodes are configured for sensing electrical activity from cardiac chamber muscle.

6. The system according to claim 4 wherein the at least two electrodes are configured for bidirectional communication with at least one other device.

7. The system according to claim 1 further comprising:
   the leadless cardiac pacemaker configured for leadless triggered left-ventricular pacing in response to conducted signals selected from a group consisting of a signal from a separate implanted pulse generator, a signal from at least one electrode-lead of a separate implanted pulse generator, a right-ventricular pacing pulse delivered by an implanted pulse generator, an atrial pacing pulse delivered by an implanted pulse generator, a signal delivered in combination with a cardioversion function, and a signal delivered in combination with a defibrillation function.

8. The system according to claim 1 further comprising:
   the leadless cardiac pacemaker configured to operate as a "slave" left-ventricular leadless cardiac pacemaker wherein the leadless cardiac pacemaker is triggered by an atrial pacing stimulation pulse or right-ventricular pacing stimulation pulse of the co-implanted pulse generator operative for right-ventricular and/or atrial pacing.

9. The system according to claim 1 further comprising:
the leadless pacemaker configured for implantation adjacent to the inside or outside wall of a cardiac chamber and configured for leadless conductive communication with the co-implanted pulse generator.

10. The system according to claim 1 further comprising:
the leadless pacemaker configured for left-ventricular pacing triggered by conducted communication from the co-implanted pulse generator, the left-ventricular pacing triggered by a right-ventricular pacing pulse and/or an atrial pacing pulse delivered by the co-implanted pulse generator.

11. The system according to claim 1 further comprising:
at least two electrodes abutting or adjacent to the housing and configured for delivering pulses generated by the pacing pulse generator and configured for operation as an incoming communication channel for receiving triggering information from the co-implanted pulse generator, the triggering information comprising an electrical signal resulting from a right-ventricular pacing stimulation pulse or an atrial pacing stimulation pulse of an implanted pulse generator and electrode-lead system.

12. The system according to claim 11 further comprising:
a controller coupled to the at least two electrodes adapted to examine triggering information validity and, for a valid condition, activating delivery of a pacing stimulation pulse following a predetermined delay of zero or more milliseconds.

13. The system according to claim 11 further comprising:
the incoming communication channel that communicates information selected from a group consisting of pacing rate, pulse duration, sensing threshold, delay intervals, refractory time intervals, stimulation pulse amplitudes, and parameters commonly programmed from an external programmer in a pacemaker; and
the at least two electrodes configured for operation as an outgoing communication channel adapted to communicate information encoded in at least one pulse generated by the pacing pulse generator and selected from a group consisting of programmable parameter settings, pacing and sensing event counts, battery voltage, battery current, information commonly displayed by external programmers used with pacemakers, and echoed information from the incoming channel to confirm correct programming.

14. The system according to claim 11 further comprising:
a controller coupled to the at least two electrodes adapted to examine signals received on the at least two electrodes, decode information encoded in the signals, and evaluate the decoded information for pacing pulse signature validation.

15. The system according to claim 11 further comprising:
a controller coupled to the at least two electrodes adapted to examine output pulse duration from the co-implanted pulse generator for usage as a signature for determining triggering information validity and, for a signature arriving within predetermined limits, activating delivery of a pacing pulse following a predetermined delay of zero or more milliseconds, the predetermined delay being determined from a method in a group consisting of preset at manufacture, programmed via an external programmer, and adaptively monitoring and conforming to duration of a triggering signal.

16. The system according to claim 11 further comprising:
a controller coupled to the at least two electrodes adapted to examine output pulse amplitude, duration, and rate from the co-implanted pulse generator for usage as a signature for determining triggering information validity and, for a signature arriving within predetermined limits, activating delivery of a pacing pulse following a predetermined delay of zero or more milliseconds.

17. The system according to claim 11 further comprising:
a controller coupled to the at least two electrodes adapted to trigger delivery of a left-ventricular pacing pulse from an atrial pacing pulse of the co-implanted pulse generator for cardiac resynchronization therapy (CRT) after a selected atrio-ventricular delay of 50 to 300 milliseconds, the controller further adapted to vary the atrio-ventricular delay according to time since a last delivered left-ventricular pacing pulse wherein a shorter atrio-ventricular delay is selected for a higher atrial rate.

18. A cardiac pacing system comprising:
a leadless cardiac pacemaker configured for implantation in electrical contact with a cardiac chamber and configured for receiving and evaluating triggering information from a co-implanted pulse generator via an electrical signal conducted from an atrial or ventricular pacing pulse delivered by the co-implanted implanted pulse generator, the leadless cardiac pacemaker comprising a pacing pulse generator configured to generate pulses adapted to perform cardiac pacing and pulses encoding information for transmission as communication signals during a refractory period, the leadless cardiac pacemaker configured to receive communication directly from a non-implanted programmer.

19. The system according to claim 18 further comprising:
at least one implanted leadless or electrode-lead pulse generator comprising the co-implanted pulse generator and configured to conduct signals that trigger left-ventricular pacing to the leadless cardiac pacemaker by direct conduction using modulated signals.

20. The system according to claim 18 wherein the leadless cardiac pacemaker further comprises:
a hermetic housing configured for placement on or attachment to the inside or outside of a cardiac chamber; and
at least two electrodes abutting or adjacent to the housing and configured for delivering the pulses from the pacing pulse generator and for receiving triggering signals from the co-implanted pulse generator.

21. The system according to claim 20 wherein the at least two electrodes are configured for operation as an incoming communication channel for receiving triggering signals from the co-implanted pulse generator, the triggering information comprising a signal resulting from a pulse generated by the co-implanted pulse generator.

22. The system according to claim 21 further comprising:
a controller coupled to the at least two electrodes adapted to examine triggering information validity and, for a valid condition, activating delivery of a pacing stimulation pulse following a predetermined delay of zero or more milliseconds.

23. The system according to claim 21 further comprising:
a controller coupled to the at least two electrodes adapted to examine output pulse duration from the co-implanted pulse generator for usage as a signature for determining triggering information validity and, for a signature arriving within predetermined limits, activating delivery of a pacing pulse following a predetermined delay of zero or more milliseconds, the predetermined delay being determined from a method in a group consisting of preset at manufacture, programmed via an external programmer, and adaptively monitoring and conforming to duration of a triggering signal.

24. The system according to claim 21 further comprising:
a controller coupled to the at least two electrodes adapted to examine output pulse duration, amplitude, and rate from the co-implanted pulse generator for usage as a signature for determining triggering information validity and, for a signature arriving within predetermined limits, activating delivery of a pacing pulse following a predetermined delay of zero or more milliseconds.

25. The system according to claim 21 further comprising:
a controller coupled to the at least two electrodes adapted to trigger delivery of an atrial pacing pulse in response to sensing of an atrial heartbeat in sinus rhythm and in response to detection of sinus rhythm below a selected rate for atrial triggered pacing.

26. The system according to claim 21 further comprising:
a controller coupled to the at least two electrodes adapted to limit synchronous pacing pulse delivery rate to a selected maximum rate.

27. The system according to claim 18 further comprising:
a plurality of leadless cardiac pacemakers configured for implantation in electrical contact with at least one cardiac chamber and distributed epicardially, the leadless cardiac pacemaker plurality adapted to be timed from an initial triggering pulse for generating simultaneous pulses for defibrillation or cardioversion therapy.

28. The system according to claim 1 wherein the pacing pulse generator is further configured to generate stimulation pulses encoding information for transmission as communication signals.

29. The system according to claim 1 wherein the pacing pulse generator is configured to encode programmable parameter setting information on the pulses.

* * * * *

UNITED STATES PATENT AND TRADEMARK OFFICE
CERTIFICATE OF CORRECTION

| | | |
|---|---|---|
| PATENT NO. | : 8,352,025 B2 | Page 1 of 1 |
| APPLICATION NO. | : 11/549596 | |
| DATED | : January 8, 2013 | |
| INVENTOR(S) | : Peter M. Jacobson | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 482 days.

Signed and Sealed this
Fourth Day of November, 2014

Michelle K. Lee
*Deputy Director of the United States Patent and Trademark Office*